United States Patent
Ishida et al.

(10) Patent No.: US 10,383,647 B2
(45) Date of Patent: Aug. 20, 2019

(54) MEDICAL MANIPULATOR

(71) Applicant: Karl Storz SE & Co. KG, Tuttlingen (DE)

(72) Inventors: Shinji Ishida, Fujinomiya (JP); Hiroaki Sano, Fujinomiya (JP); Tsuneyoshi Suzuki, Kanuma (JP); Hirofumi Mugishima, Utsunomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 304 days.

(21) Appl. No.: 14/511,944

(22) Filed: Oct. 10, 2014

(65) Prior Publication Data

US 2015/0032151 A1 Jan. 29, 2015

Related U.S. Application Data

(63) Continuation of application No. PCT/JP2013/060947, filed on Apr. 11, 2013.

(30) Foreign Application Priority Data

Apr. 12, 2012 (JP) .................................. 2012-090797

(51) Int. Cl.
*A61B 17/00* (2006.01)
*A61B 17/29* (2006.01)

(52) U.S. Cl.
CPC .......... *A61B 17/29* (2013.01); *A61B 17/2909* (2013.01); *A61B 2017/003* (2013.01);
(Continued)

(58) Field of Classification Search
CPC .............. A61B 17/29; A61B 2017/003; A61B 2017/00314; A61B 2017/2927;
(Continued)

(56) References Cited

U.S. PATENT DOCUMENTS 5,314,445 A * 5/1994 Heidmueller nee Degwitz .......... A61B 17/320016
606/174
7,549,998 B2 * 6/2009 Braun .................... A61B 17/29
606/205
(Continued)

FOREIGN PATENT DOCUMENTS

JP 4391762 B2 12/2009
JP 2012061593 A 3/2012

OTHER PUBLICATIONS

European Search Report Application No. EP 13 77 4991 Completed: Aug. 4, 2015; dated Aug. 13, 2015 6 pages.

*Primary Examiner* — Darwin P Erezo
*Assistant Examiner* — Martin T Ton
(74) *Attorney, Agent, or Firm* — Whitmyer IP Group LLC

(57) ABSTRACT

This medical manipulator is provided with: an opening/closing drive transmission unit that transmits driving force for an opening/closing operation to a tip operation section from a handle side; and a rotary driving transmission unit that transmits rotary force for a rolling operation to the tip operation section from the handle. The rotary driving transmission unit has: a rolling drive transmission tube disposed rotatably within a shaft; a bevel gear provided to the joint between the shaft and the tip operation section; and a rotating sleeve that meshes with the bevel gear. A pull-wire having flexibility and configuring a portion of the opening/closing drive transmission unit extends through the inside of the joint to the inside of the tip operation section.

15 Claims, 18 Drawing Sheets

(52) U.S. Cl.
CPC .............. *A61B 2017/00314* (2013.01); *A61B 2017/00398* (2013.01); *A61B 2017/00477* (2013.01); *A61B 2017/2927* (2013.01); *A61B 2017/2929* (2013.01); *A61B 2017/2936* (2013.01); *A61B 2017/2939* (2013.01); *A61B 2017/2946* (2013.01); *A61B 2017/2947* (2013.01)

(58) Field of Classification Search
CPC .... A61B 2017/2929; A61B 2017/2939; A61B 2017/2947; A61B 2017/293; A61B 2017/2902; A61B 2017/2908; A61B 2017/2932; A61B 2017/2933; A61B 2017/2934; A61B 2017/2037
USPC ......................................................... 606/205
See application file for complete search history.

(56) References Cited

U.S. PATENT DOCUMENTS

| | | | |
|---|---|---|---|
| 2004/0225323 A1 | 11/2004 | Nagase et al. | |
| 2008/0147113 A1* | 6/2008 | Nobis ................... | A61B 17/29 606/205 |
| 2009/0112229 A1* | 4/2009 | Omori ................... | A61B 17/29 606/130 |
| 2009/0299143 A1* | 12/2009 | Conlon ................. | A61B 17/29 600/153 |
| 2010/0076483 A1* | 3/2010 | Imuta .................... | A61B 34/70 606/205 |

* cited by examiner

MEDICAL MANIPULATOR

FIELD OF THE INVENTION

The present invention relates to a medical manipulator that is used when a surgical operation, and in particular an endoscopic surgical operation, is carried out, and in which a distal end working unit thereof having an end effector can be subjected to a rolling operation within an unlimited range of rotation.

BACKGROUND OF THE INVENTION

In an endoscopic surgical operation (also referred to as laparoscopic surgery), a plurality of holes are punctured in the abdomen of a patient, trocars (tubular instruments) are inserted through the holes, and a laparoscope (camera) and a plurality of forceps are inserted into the body cavity via each of the trocars. Grippers, scissors, and blades of an electrosurgical knife for gripping biological tissue are mounted to the tip of the forceps as an end effector.

The laparoscope and the forceps are inserted into the body cavity, and then an operator operates with the forceps while viewing a state of the inner portion of the abdominal cavity, which is shown on a monitor that is connected to the laparoscope. Since the surgical procedure does not require a laparotomy, the burden on the patient is decreased, which reduces the number of days for postoperative recovery and leaving the hospital. For this reason, the fields that such an operative method can be applied to are expected to expand.

Other than typical forceps that are not provided with joints at distal end portions thereof, as forceps that are inserted through a trocar, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is achieved in the body cavity, and manual procedures are made easy. Thus, there are a large number of medical cases to which the medical manipulator may be applied.

SUMMARY OF THE INVENTION

Incidentally, in the medical manipulator, it is desirable for the distal end working unit including the end effector to have a high degree of freedom and to have a movable range that is as wide as possible. For example, if the range of rotation of the rolling operation of the distal end working unit were unlimited, such a feature could be expected to contribute to the smooth performance of procedures such as ligation or the like. On the other hand, in the distal end working unit, in the case that a structure is maintained, which is capable of effecting an opening and closing operation as well as a tilting operation, and which further enables a rolling operation having an unlimited range of rotation, the structure of the distal end working unit tends to become complex.

The present invention has been devised while taking into consideration the aforementioned problems, and has the object of providing a medical manipulator in which, without increasing the complexity of the mechanism of the distal end working unit, a structure can be maintained that enables an opening and closing operation as well as a tilting operation of the distal end working unit, while also enabling a rolling operation having an unlimited range of rotation.

To realize the above object, the medical manipulator according to the present invention includes a handle, a shaft that extends from the handle, a distal end working unit having an end effector capable of performing an opening and closing operation, and which is connected tiltably with respect to the shaft, and further which is capable of performing a rolling operation, an opening and closing drive transmission part that transmits a driving force for performing the opening and closing operation from the handle to the distal end working unit, and a rotating drive transmission part for transmitting a rotational force for performing the rolling operation from the handle to the distal end working unit. The rotating drive transmission part includes a rolling drive transmission pipe, which extends along a direction of extension of the shaft and is rotatably disposed in the interior of the shaft, an intermediate member, which is disposed in a joint between the shaft and the distal end working unit, meshes with the rolling drive transmission pipe, and is rotatable about a tilting fulcrum of the distal end working unit, and a distal end side rotating body, which is disposed in the distal end working unit, meshes with the intermediate member, and is rotatable about a roll axis. The opening and closing drive transmission part is arranged inside the rolling drive transmission pipe, and a portion of the opening and closing drive transmission part that is inserted at least through the joint is flexible.

According to the structure of the above invention, transmission of the rotational force from the main body portion to the distal end working unit is not carried out through a wire and a pulley, but rather is carried out through the rolling drive transmission pipe. Therefore, the distal end working unit can be operated to roll over an unlimited range of rotation. Further, because the opening and closing drive transmission part is inserted through the rolling drive transmission pipe, the opening and closing driving force can be transmitted appropriately to the end effector without being influenced by rotation of the rolling drive transmission pipe. Furthermore, in the opening and closing drive transmission part, since the portion corresponding to the joint is flexible, with a simple structure, the opening and closing driving force can be transmitted appropriately to the end effector. Accordingly, in the medical manipulator of the present invention, without increasing the complexity of the mechanism of the distal end working unit, a structure can be maintained that enables the opening and closing operation as well as the tilting operation of the distal end working unit, while also realizing a rolling operation having an unlimited range of rotation.

In the above-described medical manipulator, the opening and closing drive transmission part may be capable of making advancing and retracting movements with respect to the shaft, and the end effector may perform the opening and closing operation by the advancing and retracting movements. Further, in the vicinity of the tilting fulcrum with respect to the shaft of the distal end working unit, guide members for guiding the opening and closing drive transmission part may be disposed on both sides of the opening and closing drive transmission part in the tilting direction of the distal end working unit.

According to the above structure, when the distal end working unit is bent with respect to the shaft, the opening and closing drive transmission part is supported by the guide members, whereby the bent portion of the opening and closing drive transmission part is supported in the vicinity of the tilting fulcrum of the distal end working unit. Therefore, when the distal end working unit is bent (inclined) with respect to the shaft, within the distal end working unit, advancing of the distal end of the opening and closing drive transmission part can be prevented or suppressed. Thus, the gripped condition of the target object by the end effector can suitably be maintained.

In the above-described medical manipulator, the guide members may be guide rollers.

By such a structure, even if an opening and closing drive transmission part is subjected to advancing and retracting movements under a condition in which the distal end working unit is bent with respect to the shaft, since the guide rollers are rotated accompanying the advancing and retracting movements of the opening and closing drive transmission part, the opening and closing drive transmission part can be advanced and retracted smoothly. Accordingly, the end effector can be opened and closed reliably, and operability thereof is excellent.

In the above-described medical manipulator, the joint may include a pair of joint pins arranged on a tilt axis, and the opening and closing drive transmission part may be capable of advancing and retracting in a direction intersecting an axial direction of the joint pins, through a gap that is provided between the pair of joint pins.

According to the above structure, the arrangement space for the opening and closing drive transmission part can easily be assured in the interior of the joint.

According to the medical manipulator of the present invention, without increasing the complexity of the mechanism of the distal end working unit, a structure can be maintained that enables the opening and closing operation as well as the tilting operation of the distal end working unit, while also realizing a rolling operation having an unlimited range of rotation.

DETAILED DESCRIPTION OF THE INVENTION

Hereinafter, a preferred embodiment of a medical manipulator according to the present invention will be described in detail below with reference to the accompanying drawings.

Figure 1:
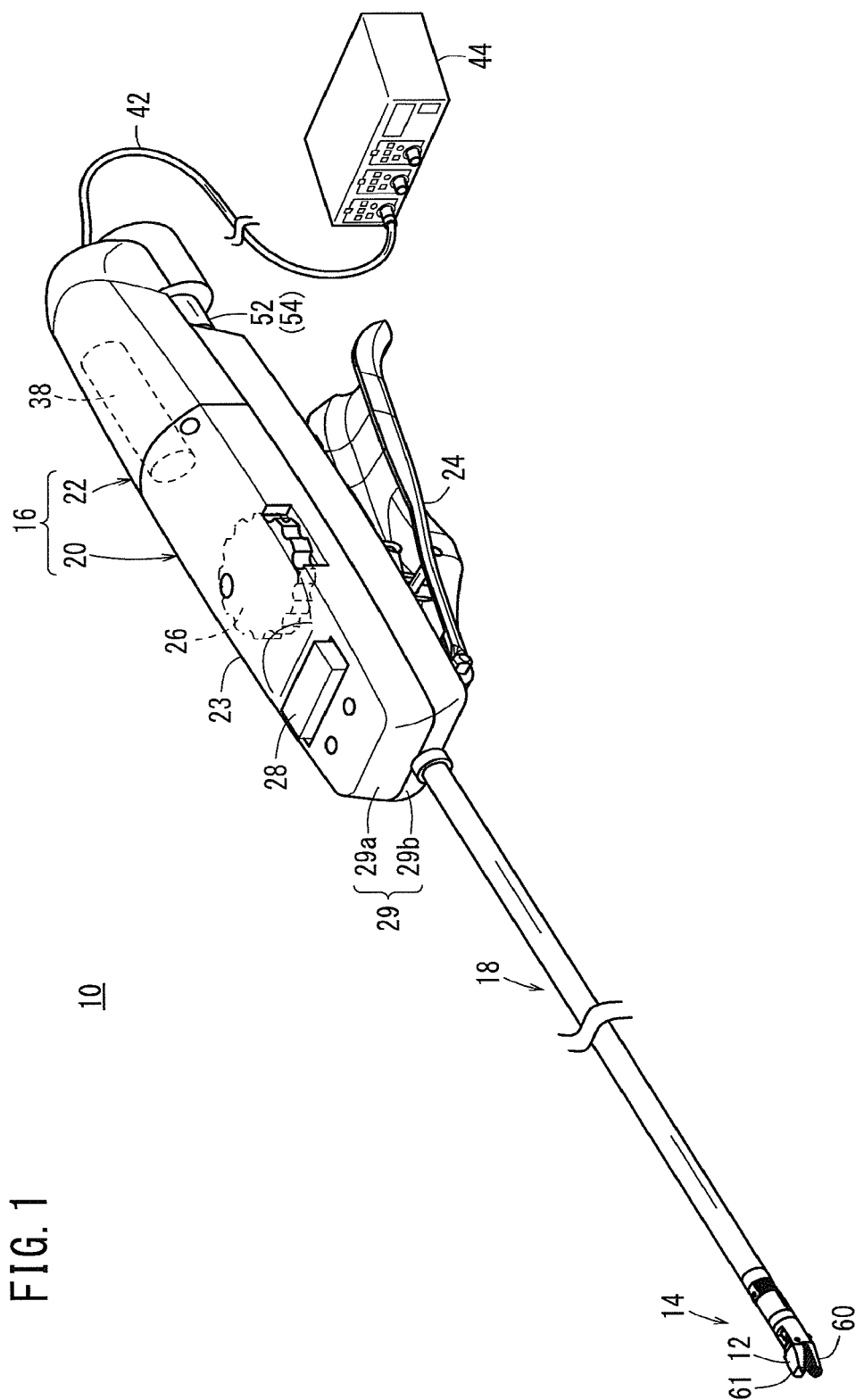
FIG. 1 is a perspective view of a medical manipulator according to an embodiment of the present invention.

FIG. 1 is a perspective view of a medical manipulator 10 according to an embodiment of the present invention. The medical manipulator 10 is a medical implement that grips a needle and a suture thread or a part of the living body or touches the living body using an end effector 12 provided at the distal end thereof, and carries out a predetermined treatment. Corresponding to the type of end effector 12 provided at the distal end, the medical manipulator 10 can be configured to have a needle driver, a grasping forceps, a monopolar electrosurgical knife, a bipolar electrosurgical knife, or the like. Below, initially, the structure of a medical manipulator 10 in which a needle driver is used as an embodiment will be described in outline, followed by a detailed description of the structure of respective parts thereof.

The medical manipulator 10 is equipped with a distal end working unit 14 including an end effector 12, a handle 16 that drives the end effector 12, and a shaft 18 that interconnects the end effector 12 and the handle 16. The end effector 12 is a portion that carries out a surgical treatment, and in the illustrated example, the end effector 12 includes a pair of gripper members 60, 61, and is configured to have a gripper mechanism that carries out an opening and closing operation on the basis of a predetermined opening and closing operating shaft. The end effector 12 is not limited to a gripper mechanism, and may be configured to have scissors or an electrode for an electrosurgical knife.

The posture of the distal end working unit 14 including the end effector 12 can be changed at a plurality of degrees of freedom with respect to the shaft 18. In the present embodiment, the distal end working unit 14 can carry out a "tilting operation" (swinging operation) in which the distal end working unit 14 is operated to tilt in left and right directions with respect to an axis of the shaft 18, and a "rolling operation" in which the distal end working unit 14 is rotated about the axial line in the longitudinal direction of the distal end working unit 14. Instead of swinging in left and right directions, the tilting operation may be an operation in which the distal end working unit 14 is operated in a tilting manner in upward and downward directions with respect to the axis of the shaft 18.

The shaft 18 is an elongated and small diameter tubular member. A plurality of members configured to make up a power transmission mechanism are inserted into and are arranged in a hollow portion of the shaft 18. Such a power transmission mechanism transmits, from the handle 16 to the distal end working unit 14, power that is necessary for carrying out the opening and closing operation of the end effector 12, and the rolling operation and the tilting operation of the distal end working unit 14.

The handle 16 includes a handle main body 20 including a plurality of operating units, and a drive unit 22 including a motor 38 and which is capable of being attached to and detached from the handle main body 20. When the motor 38 is driven in a state in which the drive unit 22 is mounted on the handle main body 20, a driving force from the motor 38 is transmitted to the distal end working unit 14. Thus, the form of use of the medical manipulator 10 can be one in which, concerning a manipulator main body thereof, which includes the handle main body 20, the shaft 18, and the distal end working unit 14, the manipulator main body can be discarded after being used a predetermined number of times, whereas the drive unit 22 can be used repeatedly many times by changing the manipulator main body that is connected to the drive unit 22.

In the medical manipulator 10 according to the present embodiment, the rolling operation is effected by an electrical drive provided through the motor 38, and the tilting operation is effected by a manual drive. However, in a modification of the medical manipulator 10, conversely, a configuration may be adopted in which the tilting operation is effected by an electrical drive provided through the motor 38, and the rolling operation is effected by a manual drive. In this manner, since a structure is provided in which either one of the tilting operation and the rolling operation is set into motion by the drive source, and both the tilting operation and the rolling operation are not effected by an electrical drive, compared to a structure in which both the tilting operation and the rolling operation are carried out by electrical drives, a reduction in size and weight can be realized by adopting such a structure including one drive source.

The handle main body 20 comprises a body portion 23 that is connected to a proximal end of the shaft 18, a lever 24 (opening and closing operating unit) provided on the body portion 23, a tilt wheel 26 (tilt operating unit) provided on the body portion 23, and a rolling switch 28 (rolling operating unit) provided on the body portion 23.

The body portion 23 makes up a part that is gripped by a user when the medical manipulator 10 is used. In the present embodiment, the body portion 23 is constituted in the form of a stick that extends over a certain length in the axial direction of the shaft 18. The body portion 23 includes a casing 29 made up from an upper cover 29a and a lower cover 29b, with drive components such as pulleys, gears, wires, etc., being arranged in the interior of the casing 29.

A lever 24 for performing an opening and closing operation of the end effector 12 is disposed on a lower part of the body portion 23, and is swingably mounted upward and downward about the distal end side thereof which serves as a support point or fulcrum. According to the present embodiment, the lever 24 is constructed as a manual manipulating element, in which an opening and closing operation of the end effector 12 is carried out by mechanically transmitting, to the end effector 12 of the distal end working unit 14, an operating force applied with respect to the lever 24. More specifically, a structure is provided in which the end effector 12 is opened when the lever 24 is opened, and the end effector 12 is closed when the lever 24 is closed.

The tilt wheel 26 for carrying out a tilting operation of the distal end working unit 14 is disposed near the center in the longitudinal direction of the body portion 23. The tilt wheel 26 is constituted as a manual manipulating element, having a portion in the circumferential direction thereof that is exposed from the casing 29. When the tilt wheel 26 is operated by being rotated, the operating force applied thereto is transmitted mechanically to the distal end working unit 14 through a tilting operation power transmission system, which is disposed internally in the handle 16 and the shaft 18, whereupon the distal end working unit 14 is tilted in a non-parallel direction (in left and right directions or upward and downward directions) with respect to the axis of the shaft 18.

Figure 15:
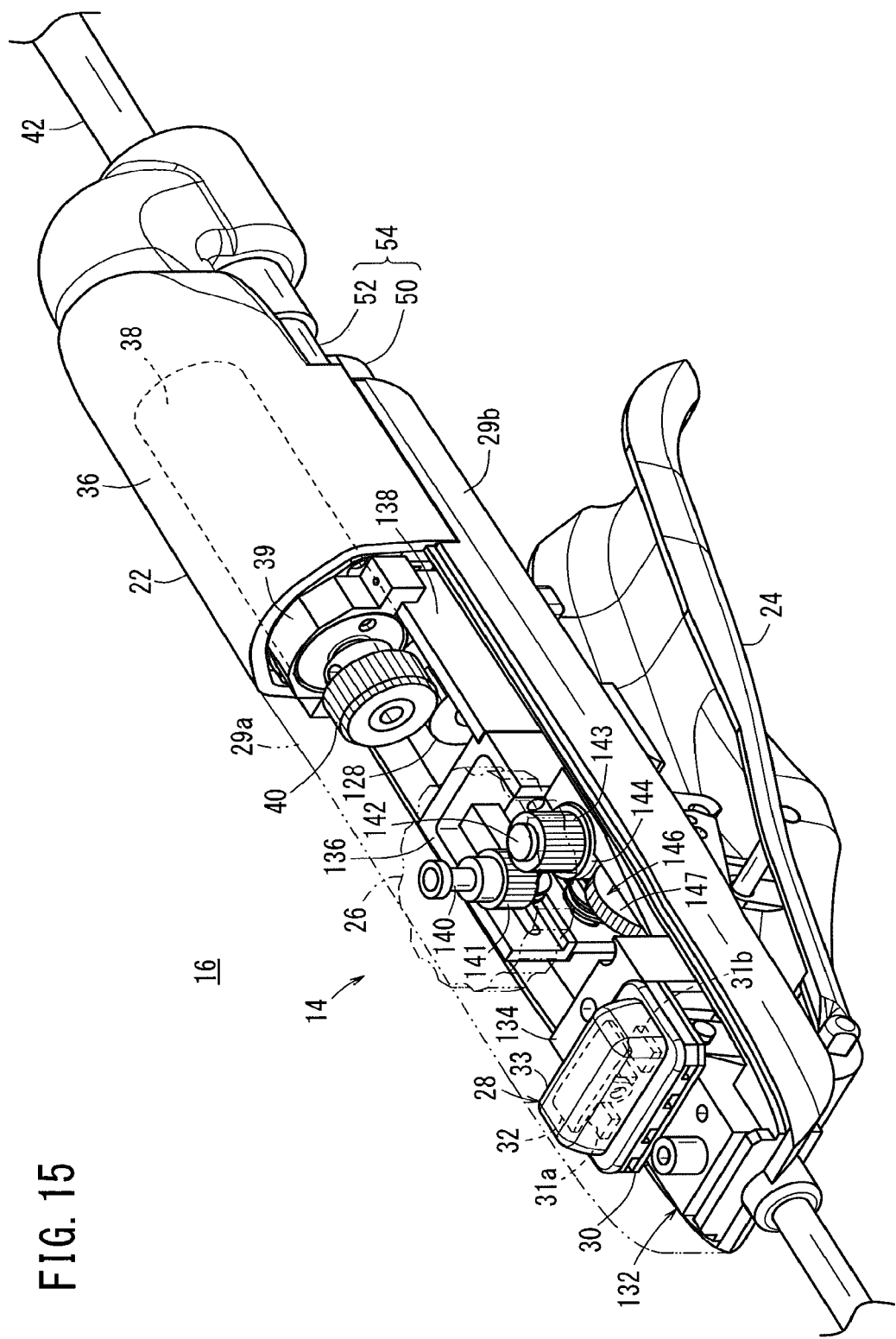
FIG. 15 is a perspective view of a handle.

The rolling switch 28 for carrying out a rolling operation of the distal end working unit 14 is disposed on an upper portion in the vicinity of the front end of the body portion 23. In the present embodiment, the rolling switch 28 is constituted as an electrical manipulating element, which supplies an operating command to the motor 38 through a controller 44. As shown in FIG. 15, the rolling switch 28 comprises a switch circuit board 30, tact switches 31a, 31b disposed on the switch circuit board 30, a switch plate 32 that is capable of being tilted with respect to the switch circuit board 30, and a switch cover 33 constituted from a flexible material (e.g., a resin or the like).

Referring again to FIG. 1, when the rolling switch 28 is pressed, a signal corresponding to the pressed position is transmitted to the controller 44 through a connector 54 and a cable 42, and under the control of the controller 44, the motor 38 is driven and a driving force from the motor 38 is transmitted to the distal end working unit 14, whereby the distal end working unit 14 is rotated about the longitudinal axis of the distal end working unit 14. In the present embodiment, the distal end working unit 14 is rotated to the right when a right-hand part of the rolling switch 28 is pressed, and the distal end working unit 14 is rotated to the left when a left-hand part of the rolling switch 28 is pressed.

Figure 2:
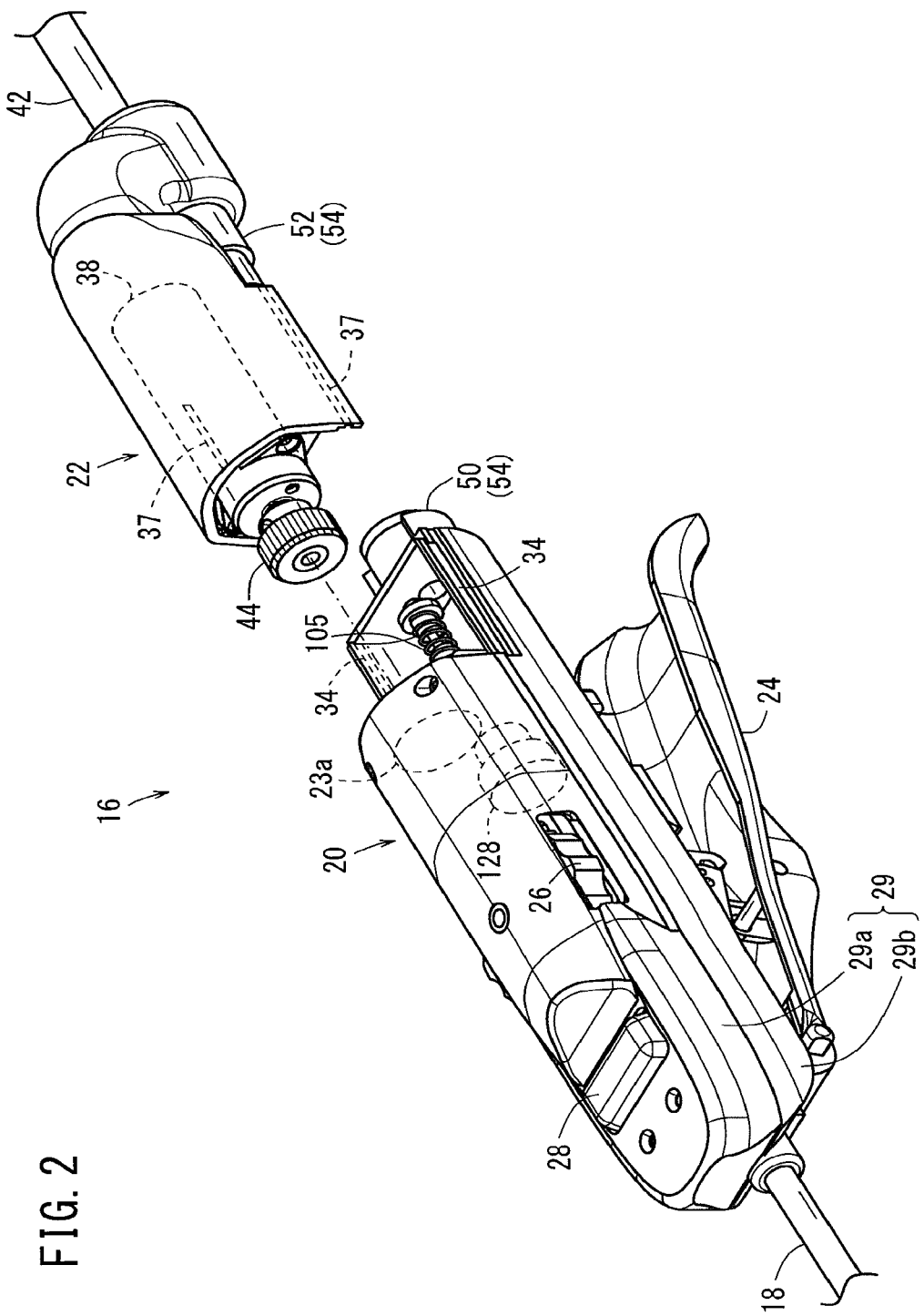
FIG. 2 is a perspective view showing a condition in which a drive unit is removed from a handle main body.
Figure 3:
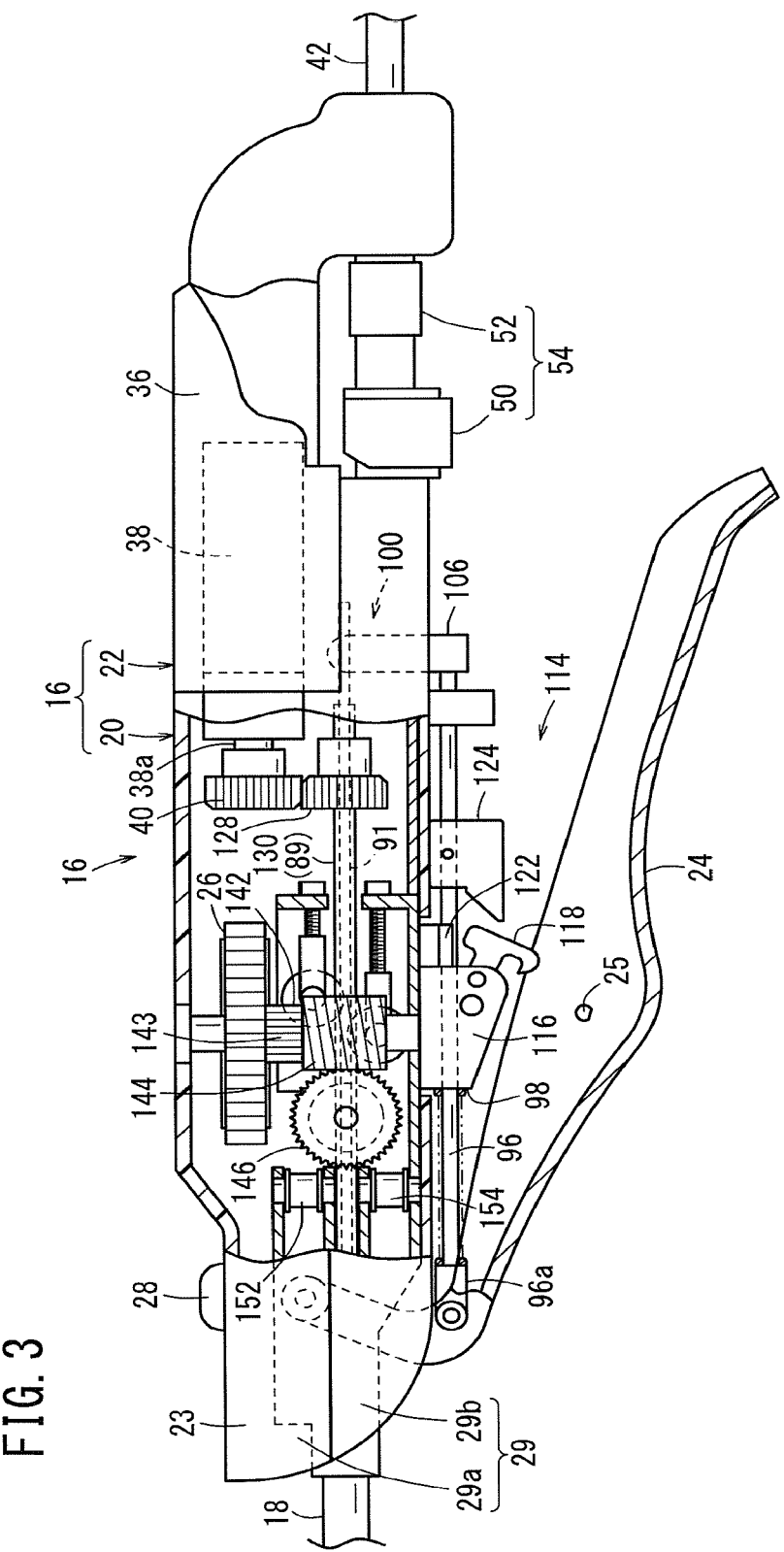
FIG. 3 is a side view partially shown in cross section of a handle of the medical manipulator.

As shown in FIGS. 2 and 3, the drive unit 22 includes a housing 36, a motor 38 (drive source) disposed inside the housing 36, and a drive gear 40 (pinion gear) which is fixed to an output shaft of the motor 38. The drive unit 22 is detachable from the rear of the handle main body 20. In a condition in which the drive unit 22 is attached (connected) to the handle main body 20, the housing 36 forms a portion that makes up the casing 29 of the handle 16 together with the handle main body 20. In the present embodiment, the housing 36 extends over a certain length in the longitudinal direction of the handle main body 20. The motor 38 is fixed to the housing 36 by a motor holder. The drive gear 40, which is fixed to the output shaft of the motor 38, projects toward the distal end side more than the distal end of the housing 36.

The drive unit 22 is connected to the controller 44 through a cable 42 that includes a power line and a signal line. The controller 44 controls the supply of power and driving of the motor 38, and receives electrical power from an external power source. When the rolling switch 28 is operated, a signal corresponding to the operation thereof is transmitted to the controller 44, and the controller 44 controls driving of the motor 38. Some or all of the functions of the controller 44 may be incorporated integrally in the drive unit 22.

An opening 23a, through which the drive gear 40 that is fixed to the output shaft of the motor 38 is capable of passing, is provided in the body portion 23 of the handle main body 20. The drive gear 40 can enter into the body portion 23 through the opening 23a. Upon attachment of the drive unit 22 to the body portion 23 of the handle main body 20, the drive gear 40, which is fixed to the output shaft 38a of the motor 38, is brought into meshing engagement with a driven gear 128 that is disposed inside the body portion 23. In this condition, when the motor 38 is rotated, the rotary driving force of the motor 38 is transmitted to the side of the handle main body 20 through the drive gear 40 and the driven gear 128.

On both sides on the rear of the body portion 23 of the handle main body 20, a handle side slide guide 34 is provided that extends in a longitudinal direction of the handle main body 20. On both sides on the front of the housing 36 of the drive unit 22, a unit side slide guide 37 is provided that extends in a longitudinal direction of the housing 36. When the drive unit 22 is connected to the handle main body 20, the drive unit 22 is moved toward the body portion 23 from the rear of the body portion 23 of the handle main body 20, and the unit side slide guide 37 and the handle side slide guide 34 are brought into engagement. In addition, under a guiding action of the guide members, when the drive unit 22 is pressed in with respect to the handle main body 20 to the maximum extent, the drive gear 40 and the driven gear 128 mesh with each other.

As shown in FIG. 3, in relation to the movement direction of the drive unit 22 relative to the handle main body 20 when the drive unit 22 is installed on the handle main body 20, the front outer peripheral edge portion of the drive gear 40 is formed in a tapered shape that decreases in diameter toward the front side, and the rear outer peripheral edge portion of the driven gear 128 is formed in a tapered shape that decreases in diameter toward the rear side.

In the present embodiment, when the drive unit 22 is installed on the handle main body 20, the movement direction of the drive unit 22 relative to the handle main body 20 is a forward direction toward the front in the longitudinal direction of the handle main body 20. The distal outer peripheral edge portion of the drive gear 40 is formed in a tapered shape that decreases in diameter toward the distal end side, and the proximal outer peripheral edge portion of the driven gear 128 is formed in a tapered shape that decreases in diameter toward the proximal end side. By such a structure, when the drive unit 22 is installed on the handle main body 20, in accordance with a guiding action performed by the tapered shape of the drive gear 40 and the tapered shape of the driven gear 128, enmeshing of the drive gear 40 and the driven gear 128 is carried out smoothly, and therefore, the installation operation can be performed quickly.

As shown in FIG. 3, a handle side connector 50 is disposed on the rear of the body portion 23 of the handle main body 20, and a unit side connector 52 is disposed on the rear of the drive unit 22. In a condition in which the drive unit 22 is attached to the handle main body 20, the handle side connector 50 and the unit side connector 52 are mutually connected electrically to each other. More specifically, the connector 54 is constituted from the handle side connector 50 and the unit side connector 52. If the rolling switch 28 is operated in a condition in which the handle side connector 50 and the unit side connector 52 are connected, a signal corresponding to the state of the rolling switch 28 is transmitted to the controller 44 through the connector 54 and the signal line of the cable 42, and under the control of the controller 44, the motor 38 that is mounted in the drive unit 22 is driven.

Figure 4:
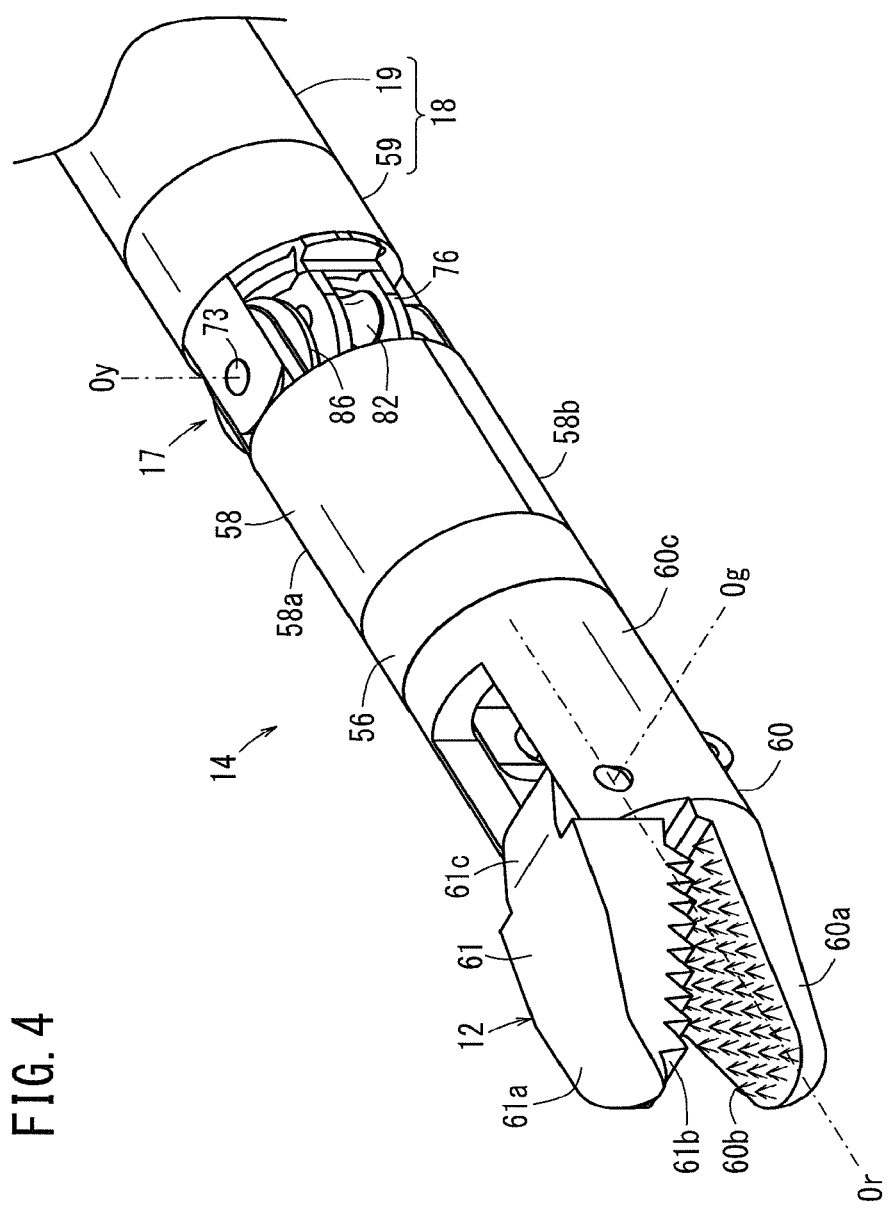
FIG. 4 is a perspective view of a distal end working unit.
Figure 5:
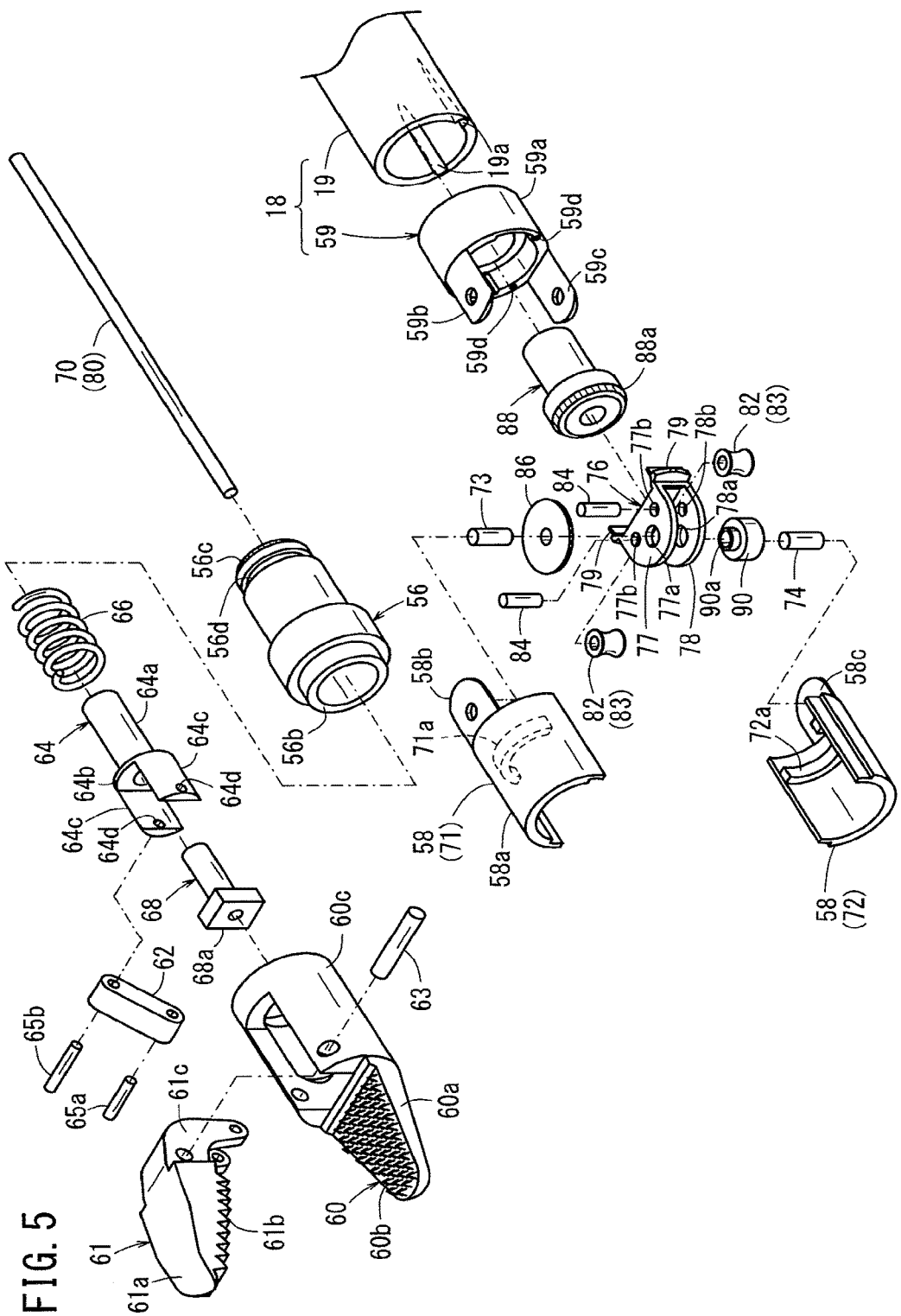
FIG. 5 is an exploded perspective view of the distal end working unit.
Figure 6:
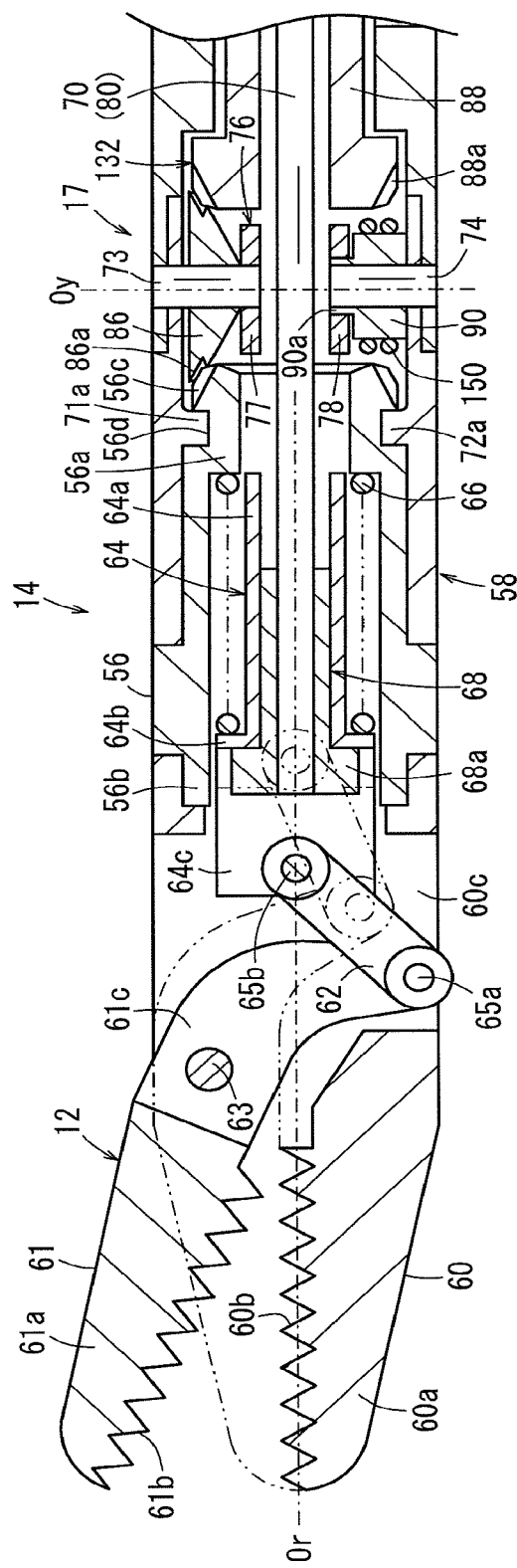
FIG. 6 is a vertical cross-sectional view of the distal end working unit.

FIG. 4 is a perspective view showing the distal end working unit 14, which is connected to the distal end of the shaft 18. FIG. 5 is an exploded perspective view of the distal end working unit 14. FIG. 6 is a vertical cross-sectional view of the distal end working unit 14. As shown in FIGS. 4 through 6, the distal end working unit 14 includes the end effector 12 that is capable of being opened and closed, a rotating sleeve 56 (distal end side rotating body) of a hollow cylindrical shape, to which the end effector 12 is fixed, and a distal end side fulcrum block 58 that rotatably supports the rotating sleeve 56 in an axially rotatable manner.

The end effector 12 is made up from a first gripper member 60 and a second gripper member 61. The first gripper member 60 and the second gripper member 61 are connected by a pin 63 so as to be capable of rotating about a gripper axis Og. A gripping face 60b, which is formed with a large number of irregularities thereon for providing a non-slip surface, is formed on a jaw portion 60a of the first gripper member 60. Similarly, a gripping face 61b, which is formed with a large number of irregularities thereon for providing a non-slip surface, is formed on a jaw portion 61a of the second gripper member 61. A base portion 60c of the first gripper member 60 is substantially hollow cylindrical in shape, and on the base portion 60c, a base portion 61c of the second gripper member 61 is connected by a pin 63, so as to be capable of rotating with respect thereto. An object to be gripped, for example a needle or the like, is gripped by the gripping face 60b of the first gripper member 60 and the gripping face 61b of the second gripper member 61.

The base portion 61c of the second gripper member 61 is connected through a link member 62 to a transmission member 64. The base portion 61c and the link member 62, as well as the link member 62 and the transmission member 64, are connected rotatably by respective pins 65a, 65b. The transmission member 64 includes a guide tube 64a, a flange 64b disposed on a distal end of the guide tube 64a, and support arms 64c that extend mutually in parallel in the direction of the distal end from edges of the flange 64b. The transmission member 64 is arranged in the interior of the rotating sleeve 56 so as to be movable in the axial direction. The pin 65b is fitted into pin holes 64d that are provided in the support arms 64c.

A compression spring 66 is arranged between the transmission member 64 and the rotating sleeve 56. One end of the compression spring 66 abuts against the flange 64b of the transmission member 64, whereas the other end thereof abuts against a stepped portion 56a (see FIG. 6) provided on an inner circumferential portion of the rotating sleeve 56, so that the transmission member 64 normally is elastically biased in the direction of the distal end.

An end collar 68 is inserted into the transmission member 64 from the distal end side. A distal end of the end collar 68 is constituted as an engaging bulge 68a that comes into abutment and engages with the distal end surface of the guide tube 64a of the transmission member 64. The end collar 68 is fixed to a distal end of a pull wire 70 that passes through a joint 17 (see FIGS. 4 and 6) between the distal end working unit 14 and the shaft 18.

The pull wire 70 forms a member that moves in an advancing and retracting manner in the interior of the shaft 18 and the interior of the distal end working unit 14 responsive to an operation made with respect to the lever 24 of the handle 16. When the pull wire 70 is displaced in the direction of the proximal end, the transmission member 64 is pushed toward the proximal end by the end collar 68 to which the pull wire 70 is fixed, whereby the transmission member 64 is displaced in the direction of the proximal end in opposition to the biasing force of the compression spring 66. Accompanying displacement of the transmission member 64 toward the proximal end, the second gripper member 61, which is connected to the link member 62, is rotated in a closing direction with respect to the first gripper member 60. In FIG. 6, the first gripper member 60 is shown by an imaginary line, in a state of being closed to a position at which the gripping face 61b of the second gripper member 61 and the gripping face 60b of the first gripper member 60 are placed in contact.

From the state of being closed to the position at which the gripping face 61b of the second gripper member 61 and the gripping face 60b of the first gripper member 60 are in contact, when the pull wire 70 and the end collar 68 are advanced, since the transmission member 64 is urged forward by the elastic force of the compression spring 66, the first gripper member 60 rotates through the link member 62 in a direction to open with respect to the second gripper member 61, and is restored to its original state. This operation is referred to as an opening and closing operation of the end effector 12.

In the present embodiment, for the end effector 12, a case has been described in which the first gripper member 60 is constituted as a fixed part and the second gripper member 61 is constituted as a movable part. However, both of the gripper members 60, 61 may be constituted as movable parts.

At a reduced diameter portion 56b on the distal end thereof, the rotating sleeve 56 is fitted and fixedly attached to the base portion 60c of the first gripper member 60. In the rotating sleeve 56, a bevel gear part 56c is provided on the proximal end thereof, and an annular recess 56d is disposed at a position more toward the distal end side than the bevel gear part 56c. The end effector 12, the rotating sleeve 56, the transmission member 64, the end collar 68, and the compression spring 66 are capable of rotating in unison with respect to the distal end side fulcrum block 58, about the longitudinally directed roll axis Or of the distal end working unit 14.

The distal end side fulcrum block 58 is made up from a semicircular upper block 71 and a semicircular lower block 72. The upper block 71 and the lower block 72 are assembled together to form a hollow cylindrical shape. The outer diameter of the distal end side fulcrum block 58 preferably is 3 mm to 8 mm, and in the present embodiment, a description is given in which the outer diameter thereof is 5 mm. The inner diameter of the distal end side fulcrum block 58 preferably is 2 mm to 7 mm, and in the present embodiment, a description is given in which the inner diameter thereof is 4 mm.

Respective arcuate projections 71a, 72a are provided on inner circumferential portions of the upper block 71 and the lower block 72. By engagement between the arcuate projections 71a, 72a and an annular recess 56d that is provided on the rotating sleeve 56, the rotating sleeve 56 is connected rotatably, and is immovable in the axial direction, with respect to the distal end side fulcrum block 58. The arcuate projections 71a, 72a have a predetermined amount of projection (e.g., 0.7 mm) toward the longitudinal center axis, and have a predetermined width (e.g., 1 mm) in the longitudinal direction in order to obtain sufficient strength. Further, in the present embodiment, although one arcuate projection 71a on the inner circumferential portion of the semicircular upper block 71, and one arcuate projection 72a on the inner circumferential portion of the semicircular lower block 72 are provided, the invention is not limited to this feature, and the arcuate projection 71a may be constituted from a plurality of projections. For example, the arcuate projections 71a may be arranged at intervals of 30° on the inner circumferential portion of the upper block 71. In this case, the arcuate projection 71a would be constituted from three arcuate projections.

The distal end side fulcrum block 58 and a shaft side fulcrum block 59 are connected together rotatably about the tilt axis Oy by joint pins 73, 74. The shaft side fulcrum block 59 is fixed to the distal end of the hollow shaft main body 19 that constitutes the body portion of the shaft 18. The shaft 18 is constituted from the shaft side fulcrum block 59 and the shaft main body 19.

In the present embodiment, the tilt axis Oy is set in the vertical direction. However, the tilt axis Oy may be set in a different direction that intersects the axis of the shaft main body 19. The distal end side fulcrum block 58 includes a tubular portion 58a, and tongue pieces 58b, 58c, which project mutually in parallel toward the proximal end side from upper and lower portions on the proximal end of the tubular portion 58a. The shaft side fulcrum block 59 includes a tubular portion 59a, and tongue pieces 59b, 59c, which project mutually in parallel toward the distal end side from upper and lower portions on the distal end of the tubular portion 59a. Joint pins 73, 74 are fitted into the tongue pieces 58b, 58c of the distal end side fulcrum block 58, and into the tongue pieces 59b, 59c of the shaft side fulcrum block 59.

As shown in FIGS. 5 through 9, a support block 76 is mounted on the distal end of the tubular portion 59a of the shaft side fulcrum block 59. The support block 76 includes upper and lower support plates 77, 78 that confront one another mutually in parallel, and connecting portions 79 that are connected to both left and right rear end portions of the support plates 77, 78. A pin hole 77a, into which the upper side joint pin 73 is inserted, and left and right pin holes 77b, into which upper ends of two pins 84 are inserted respectively, are provided in the upper side support plate 77. A hole 78a, into which a reduced diameter upper end portion 90a of a driven pulley 90 is inserted, and left and right pin holes 78b, into which lower ends of the two pins 84 are inserted respectively, are provided in the lower side support plate 78.

Figure 7:
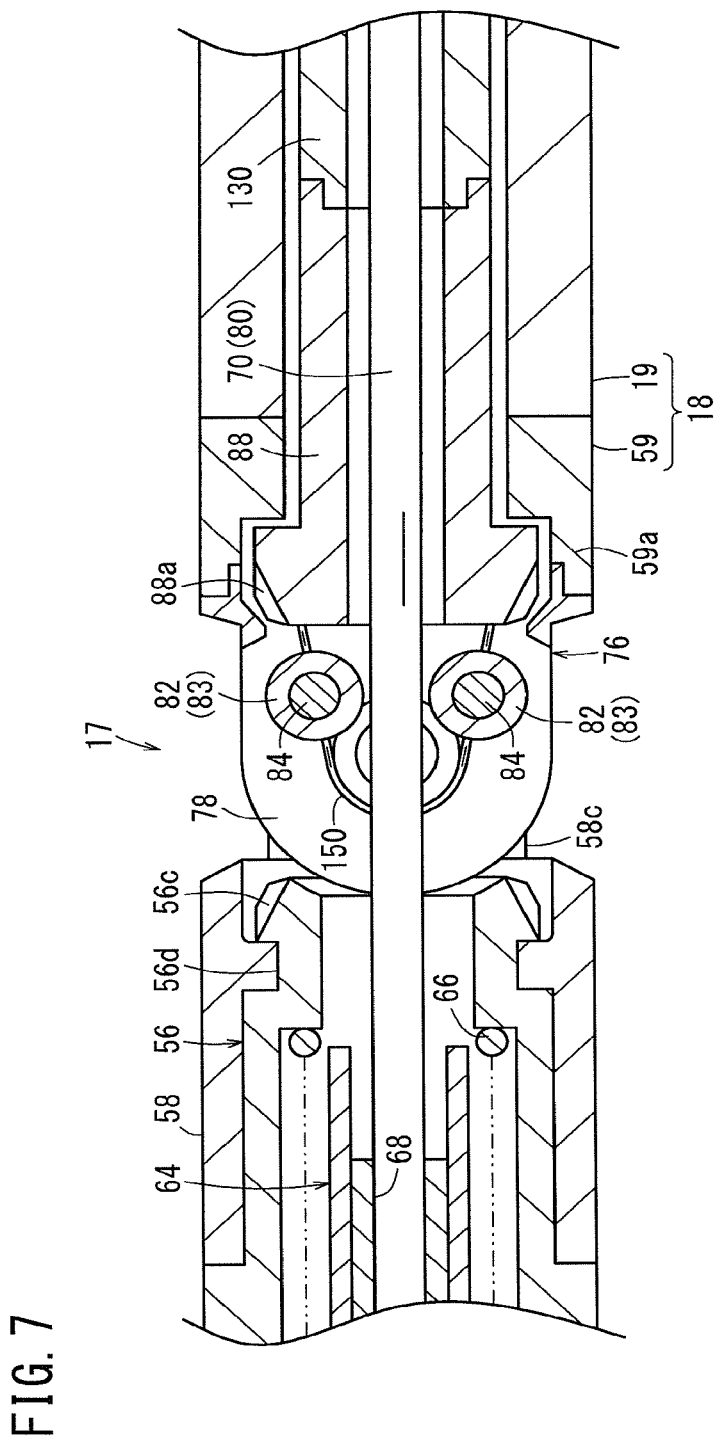
FIG. 7 is a vertical cross-sectional view of a joint and an area in the vicinity thereof, showing a state in which the distal end working unit is arranged in a straight manner with respect to a shaft.
Figure 8:
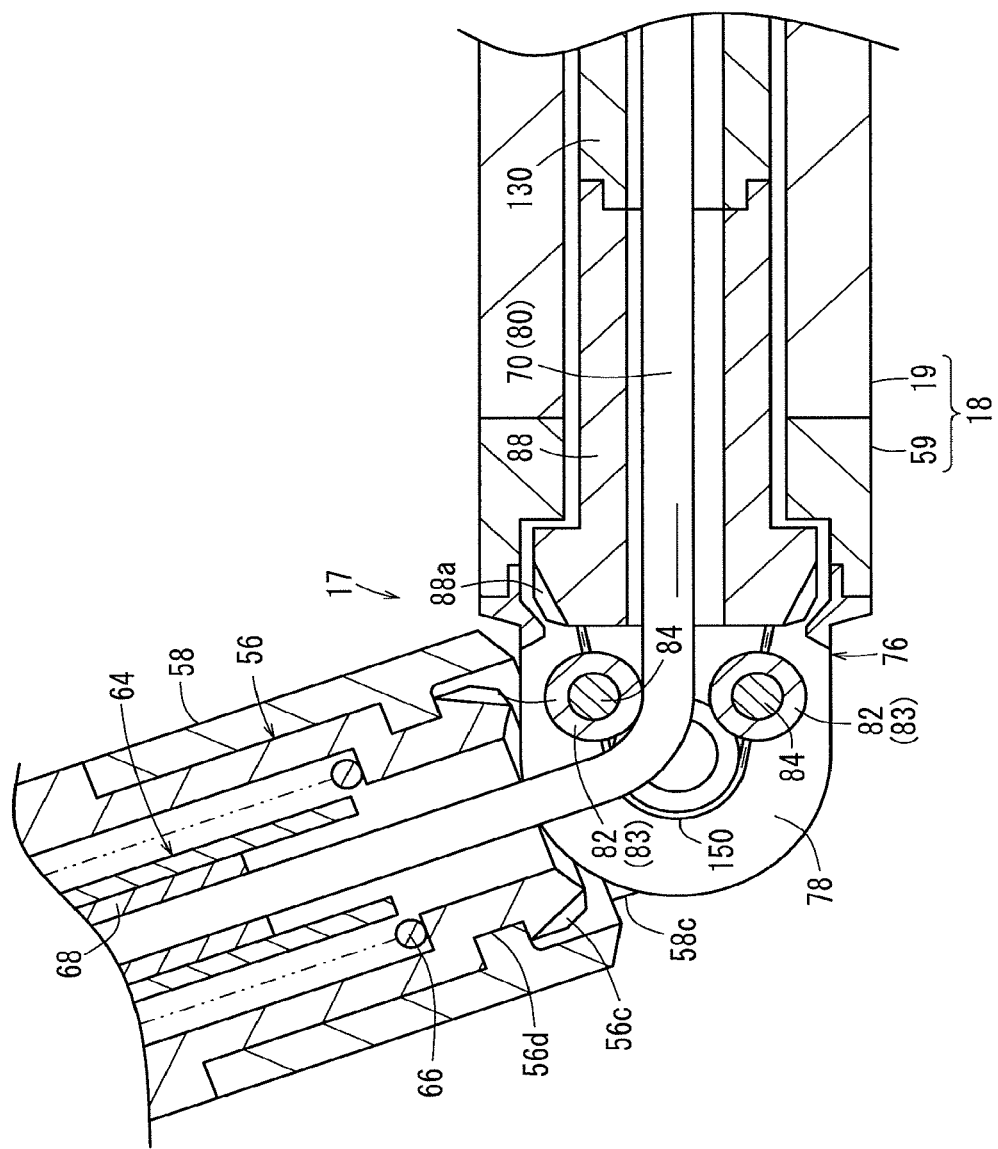
FIG. 8 is a vertical cross-sectional view of the joint and an area in the vicinity thereof, showing a condition (bent state) in which the distal end working unit is inclined with respect to the shaft.
Figure 9:
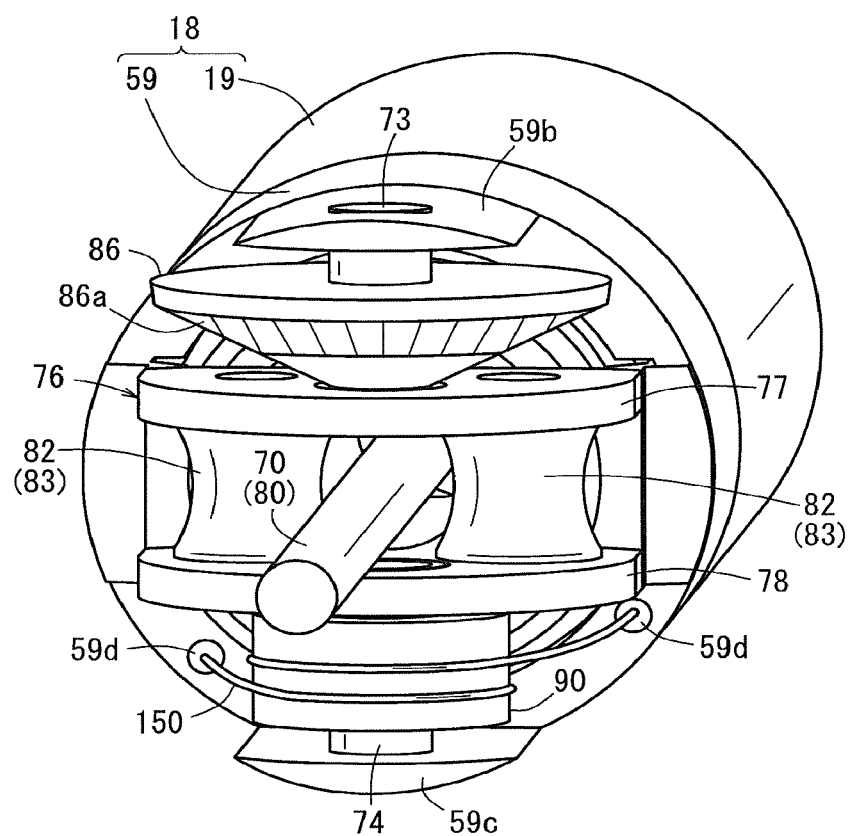
FIG. 9 is a perspective view from a front side of a guide member and an area in the vicinity thereof.

As shown in FIGS. 7 through 9, in the vicinity of the tilt axis Oy with respect to the shaft 18 of the distal end working unit 14, guide members 82 that serve to guide the pull wire 70 are disposed on both sides (in the present embodiment on both left and right sides) of the pull wire 70 (opening and closing drive transmission part 80) in the tilting direction of the distal end working unit 14. Because the guide members 82 are disposed in this manner, when the distal end working unit 14 is bent with respect to the shaft 18, the pull wire 70 is supported by the guide members 82, whereby the bent portion of the opening and closing drive transmission part 80 is supported in the vicinity of the tilting fulcrum of the distal end working unit 14. Therefore, when the distal end working unit 14 is bent (inclined) with respect to the shaft 18 (see FIG. 8), within the distal end working unit 14, advancing of the distal end of the pull wire 70 can be prevented or suppressed. Thus, the gripped condition of the target object by the end effector 12 can suitably be maintained.

In the present embodiment, as the guide members 82, two guide rollers 83 are arranged alongside each other in the left and right direction between the upper and lower support plates 77, 78. The guide rollers 83 are supported rotatably at an interval in the left and right direction by two pins 84, which are arranged mutually in parallel, and the aforementioned pull wire 70 passes between the two guide rollers 83. By such a structure, even if the opening and closing drive transmission part 80 is subjected to advancing and retracting movements under a condition in which the distal end working unit 14 is bent with respect to the shaft 18, since the guide rollers 83 are rotated accompanying advancing and retracting movements of the pull wire 70 (opening and closing drive transmission part 80), the pull wire 70 can be advanced and retracted smoothly. Accordingly, the end effector 12 can be opened and closed reliably, and operability thereof is excellent.

As shown in FIG. 6, the joint 17 that is present between the distal end working unit 14 and the shaft 18 includes the pair of joint pins 73, 74, which are arranged on the tilt axis Oy. In addition, the pull wire 70, which constitutes part of the opening and closing drive transmission part 80, is capable of advancing and retracting in a direction intersecting the axial direction of the joint pins 73, 74 through a gap that is provided between the pair of joint pins 73, 74. According to this structure, an arrangement space for the pull wire 70 can easily be assured in the interior of the joint 17.

Between the upper side support plate 77 and the tongue piece 58b, a bevel gear 86 (intermediate member) is supported rotatably by the joint pin 73. The bevel gear 86 is rotatable independently of the support plate 77 and the tongue piece 58b. The teeth 86a of the bevel gear 86 are enmeshed with the bevel gear part 56c provided on the proximal end of the rotating sleeve 56, and a bevel gear part 88a that is provided on the distal end of a gear member 88. The gear member 88 on which the bevel gear part 88a is provided is a hollow cylindrical member, with the pull wire 70 being inserted internally through the hollow portion thereof.

Upon rotation of the gear member 88, the rotational force of the gear member 88 is transmitted to the rotating sleeve 56 through the bevel gear 86 and the bevel gear part 56c, and the rotating sleeve 56 together with the end effector 12 that is fixed thereto is rotated about the roll axis Or with respect to the distal end side fulcrum block 58. This operation is referred to as a rolling operation of the distal end working unit 14.

Between the lower side support plate 78 and the tongue piece 58c, the driven pulley 90 is supported rotatably by the joint pin 74. The driven pulley 90 is fixed to an inner surface of the tongue piece 58c of the distal end side fulcrum block 58. Accordingly, the driven pulley 90 and the distal end side fulcrum block 58 including the tongue piece 58c are capable of swinging in unison with respect to the shaft side fulcrum block 59. A tilting operation wire 150 is trained around the driven pulley 90. A portion of the wire 150 is fixed to the driven pulley 90, and the wire 150 passes through the interior of the shaft 18 up to the side of the handle 16. The structural arrangement of the wire 150 will be described in detail later.

When the driven pulley 90 is driven and rotated by the wire 150, the distal end side fulcrum block 58, which is fixed to the driven pulley 90, is rotated integrally with the driven pulley 90. As a result, the distal end working unit 14 including the distal end side fulcrum block 58, the rotating sleeve 56, and the end effector 12 is rotated about the tilt axis Oy with respect to the shaft 18. This operation is referred to as a tilting operation of the distal end working unit 14. In FIG. 8, a condition is shown in which the distal end working unit 14 is inclined (bent) with respect to the shaft 18. Assuming the condition in which the distal end working unit 14 is oriented in a straight manner with respect to the shaft 18 to be a neutral position (reference position), the tilting operation of the distal end working unit 14 includes a movement range to a plus side (right side) and to a minus side (left side), respectively. In the present embodiment, the distal end working unit 14 has a movable range of +70° to −70° in relation to the tilting operation.

Figure 10:
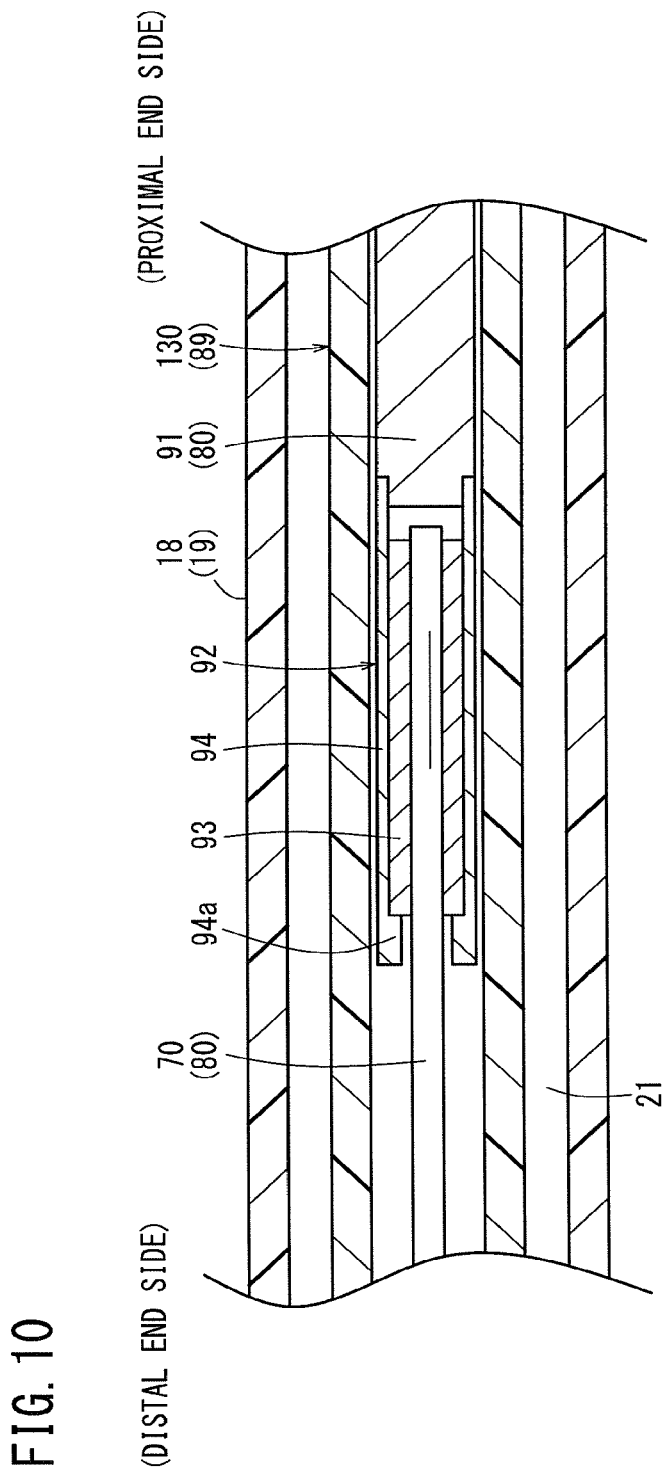
FIG. 10 is a vertical cross-sectional view showing a connecting structure of a pull wire and a pull rod and an area in the vicinity thereof.

FIG. 10 is a vertical cross-sectional view showing a connecting structure 92 between the pull wire 70 and a pull rod 91. As shown in FIG. 10, the pull wire 70 and the pull rod 91 are capable of relative rotation in the interior of a hollow shaft 89 that is connected to the proximal end of the gear member 88, and are connected so as to transmit a pull force in the direction of the proximal end of the pull rod 91 to the pull wire 70. More specifically, a wire collar 93 is fixed to the proximal end of the pull wire 70, and a hollow outer side collar 94 is fixed to the distal end of the pull rod 91, with the wire collar 93 being arranged inside the outer side collar 94. Although the wire collar 93 can rotate about the axis in the interior of the outer side collar 94, since it is hooked onto a reduced-diameter part 94a on the distal end of the outer side collar 94, the wire collar 93 does not come out from the outer side collar 94.

Due to being constructed in this manner, when the pull rod 91 is displaced in the axial direction, the pull wire 70, which is connected to the pull rod 91 through the connecting structure 92, also is displaced in the axial direction to thereby carry out the opening and closing operation of the end effector 12. Further, when the distal end working unit 14 implements the rolling operation, since the pull wire 70 can rotate with respect to the pull rod 91, the rolling operation of the distal end working unit 14 is not hindered, twisting of the pull wire 70 does not occur, and damage to the pull wire 70 can be prevented.

As shown in FIG. 3, the pull rod 91 is inserted through the interior of the hollow shaft 89, and the proximal end thereof projects outwardly from the proximal end of the hollow shaft 89. On the other hand, a distal end part of the lever 24 is connected to a location near the distal end of the body portion 23 so as to be capable of swinging with respect to the body portion 23. A distal end of a lever rod 96 is connected rotatably in the vicinity of the distal end of the lever 24. The lever rod 96 is arranged below the body portion 23 substantially in parallel with the longitudinal direction of the body portion 23. A hook holder 116 that supports a later-described hook member 118 is fixed to a lower part of the body portion 23. A compression spring 98 is arranged between a distal end surface of the hook holder 116 and a distal end expanded diameter portion 96a of the lever rod 96. The compression spring 98 normally applies an elastic biasing force to the lever rod 96 in the distal end direction. Consequently, by the elastic force of the compression spring 98, the lever 24, which is connected to the lever rod 96, normally receives a force in a direction to open with respect to the body portion 23.

Figure 11:
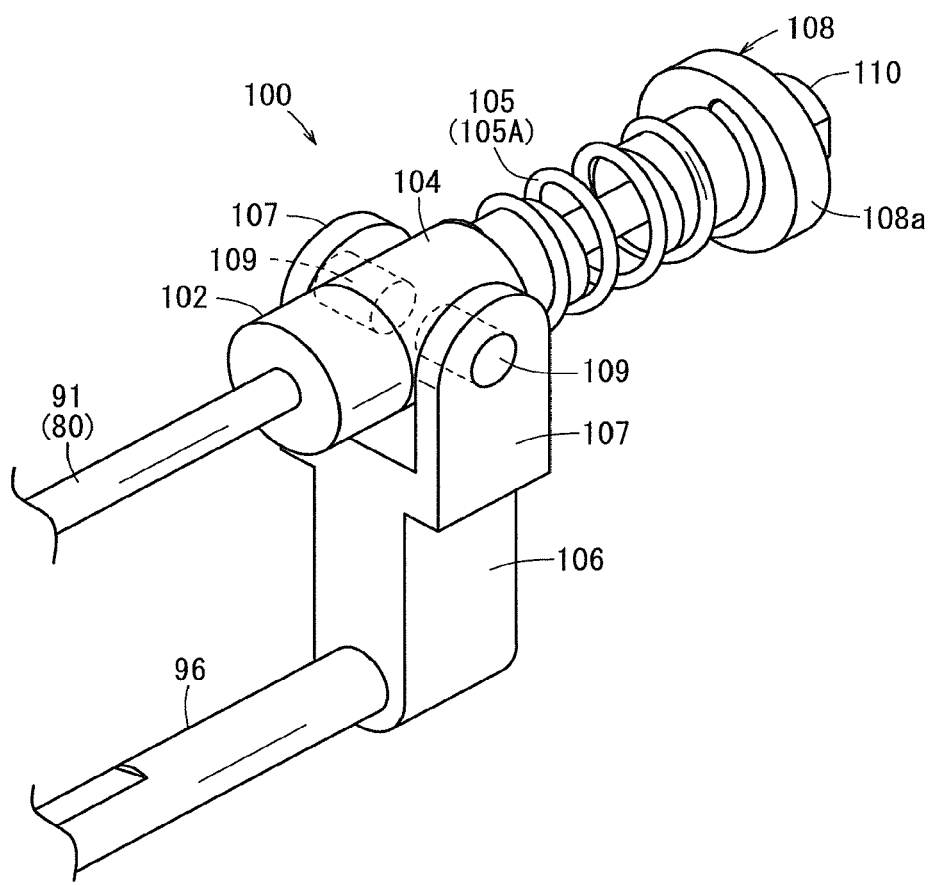
FIG. 11 is a perspective view of a load control mechanism.
Figure 12A:
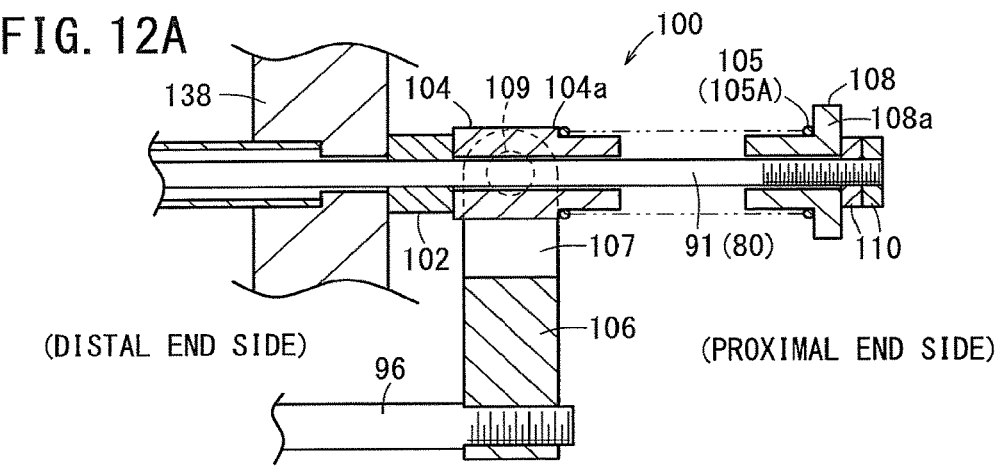
FIG. 12A is a vertical cross sectional view showing the load control mechanism.
Figure 12B:
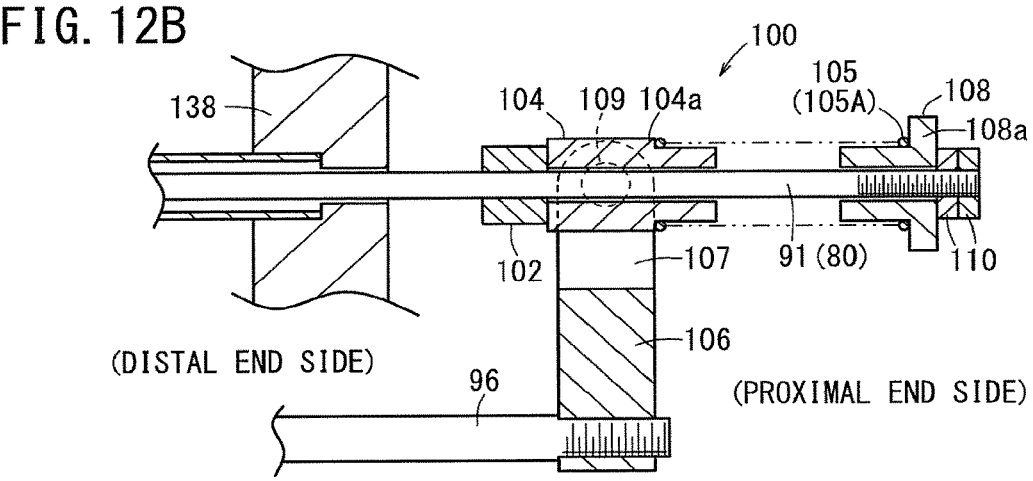
FIG. 12B is a vertical cross sectional view showing the load control mechanism, in a condition of being retracted somewhat with respect to the condition shown in FIG. 12A.
Figure 12C:
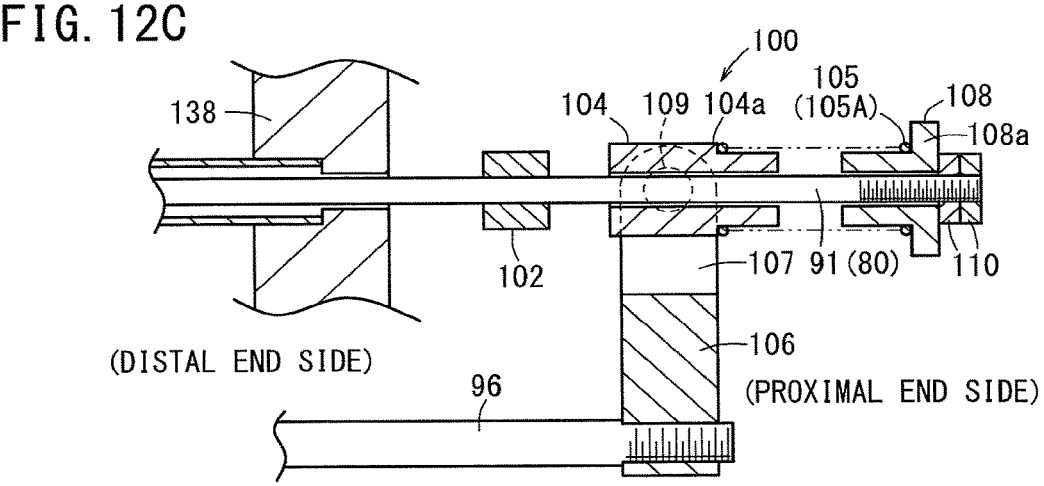
FIG. 12C is a vertical cross sectional view showing the load control mechanism, showing a condition in which the distance between a movable portion and a fixed portion thereof is shorter than in the condition shown in FIG. 12B.

FIG. 11 is a perspective view of a load control mechanism 100 that transmits a driving force from the lever 24 through an elastic member 105 to the opening and closing drive transmission part 80. FIGS. 12A through 12C are vertical cross sectional views of the load control mechanism 100 and the surrounding area thereof. The load control mechanism 100 is disposed on a driving force transmission path disposed between the opening and closing drive transmission part 80 that is made up from the pull wire 70 and the pull rod 91, and the lever 24 that functions as an operating unit.

In the present embodiment, the load control mechanism 100 is disposed on the proximal ends of the pull rod 91 and the lever rod 96, and includes an engagement portion 102 that is fixed to the pull rod 91, a movable portion 104 that is guided by the pull rod 91 and is capable of being displaced in the axial direction, a support coupling body 106 that is fixed to the lever rod 96 and is engaged with the movable portion 104, a fixed portion 108 that is positioned with respect to the pull rod 91 more on the proximal side than the movable portion 104, an elastic member 105 that is arranged between the movable portion 104 and the fixed portion 108, and an adjustment nut 110 (adjustment member) that is screw-engaged with the pull rod 91 and the position of which is displaceable in the axial direction with respect to the pull rod 91 by rotation on the pull rod 91.

The engagement portion 102 is fixed non-displaceably in the axial direction with respect to the pull rod 91, and by the movable portion 104, which is biased toward the distal end by the elastic member 105, coming into abutment against the engagement portion 102, the engagement portion 102 functions as a stopper for stopping the movable portion 104 so as not to be displaced any further toward the distal end side. The movable portion 104 is formed in a hollow cylindrical shape, and the pull rod 91 is inserted through the hollow portion thereof. The movable portion 104 normally is biased elastically in the distal end direction by the elastic member 105.

The lower end of the support coupling body 106 is fixed by screw-engagement to the proximal end of the lever rod 96. Left and right arms 107 are provided on the upper side of the support coupling body 106, and in a condition in which the movable portion 104 is disposed between the left and right arms 107, the upper end of the support coupling body 106 is connected rotatably to the movable portion 104 through a pin 109. In the present embodiment, the elastic member 105 is a coil shaped compression spring 105A, which is arranged on the outer side of the pull rod 91 between the movable portion 104 and the fixed portion 108. The elastic force of the compression spring 105A is greater than the elastic force of the compression spring 66 (see FIG. 6) that is arranged in the interior of the distal end working unit 14, so that accompanying displacement of the movable portion 104 together with the lever rod 96 in the direction of the proximal end, the pull rod 91 also is displaced in the direction of the proximal end.

The fixed portion 108 is formed in a hollow cylindrical shape, and a flange 108a that projects in a radial outward direction is disposed on the proximal end thereof. One end of the compression spring 105A abuts against a stepped part 104a provided on the movable portion 104, whereas the other end of the compression spring 105A abuts against the front surface of the flange 108a. Therefore, the compression spring 105A is maintained between the movable portion 104 and the fixed portion 108. The fixed portion 108 is stopped by abutment against the end face of the adjustment nut 110, whereby the fixed portion 108 is positioned with respect to the pull rod 91.

When the adjustment nut 110 is rotated, the position of the adjustment nut 110 in the axial direction is displaced with respect to the pull rod 91. Accordingly, by the adjustment nut 110, the position of the fixed portion 108 with respect to the pull rod 91 can be adjusted, and the fixed portion 108 can be positioned.

With the load control mechanism 100, which is constructed in the foregoing manner, the following actions are carried out. In the handle main body 20, in a condition in which the lever 24 is open with respect to the body portion 23 (see FIG. 3), the lever rod 96, the support coupling body 106, and the movable portion 104 are positioned as shown in FIG. 12A. This will be regarded as an initial position. In the initial position, the pull rod 91 is advanced to a position at which the end effector 12 is in a fully open state. When the user grips the lever 24, and pulls the lever 24 toward the side of the body portion 23 (thereby closing the lever 24), as shown in FIG. 12B, the lever rod 96, the support coupling body 106, and the movable portion 104 are displaced in the direction of the proximal end. At this time, since the pull rod 91 is pulled in the direction of the proximal end via the compression spring 105A, the movable portion 104, and the adjustment nut 110, the end effector 12 is operated in a direction to close.

From a position at which the end effector 12 has just gripped the target object, when the lever 24 is pulled toward the side of the body portion 23, as shown in FIG. 12C, by the compression spring 105A being compressed between the fixed portion 108 and the movable portion 104, the movable portion 104 is displaced toward the side of the fixed portion 108, i.e., toward the proximal end, while the positions of the pull rod 91, the fixed portion 108, and the adjustment nut 110 are held in place. At this time, the distance between the fixed portion 108 and the movable portion 104 becomes smaller than in the condition shown in FIG. 12A. By this action of the load control mechanism 100, after the end effector 12 has gripped the target object, even if the lever 24 is operated further in a direction to close the end effector 12, by the compression spring 105A being subjected to compressive deformation, an excessive pulling load is prevented from being applied to the opening and closing drive transmission part 80 (overload prevention function).

Further, according to the load control mechanism 100, in a state in which the target object has been gripped by the end effector 12, when the distal end working unit 14 is bent with respect to the shaft 18, the elastic member 105, which is disposed on the driving force transmission path between the opening and closing drive transmission part 80 and the lever 24, extends in length, whereby the pull wire 70 is displaced in the proximal end direction by an amount that compensates for any shifting in the bending direction of the pull wire 70 at the joint 17 between the distal end working unit 14 and the shaft 18. For this reason, the end effector 12 does not open accompanying bending of the distal end working unit 14. More specifically, the gripped condition of the target object by the end effector 12 can reliably be maintained (grip maintaining function).

Furthermore, in the case of the present embodiment, the coil shaped compression spring 105A is arranged to surround the outer side of the pull rod 91 that forms one part of the opening and closing drive transmission part 80, and together therewith, from the fact that the fixed portion 108 is displaced in the axial direction by being guided via the pull rod 91, since displacement of the fixed portion 108 is carried out smoothly, the aforementioned grip maintaining function and overload prevention function are securely exhibited.

Further, in the case of the present embodiment, by changing the position of the adjustment nut 110 with respect to the pull rod 91 that makes up the opening and closing drive transmission part 80, the size of the biasing force of the elastic member 105 in the load control mechanism 100 can easily be adjusted.

Figure 13:
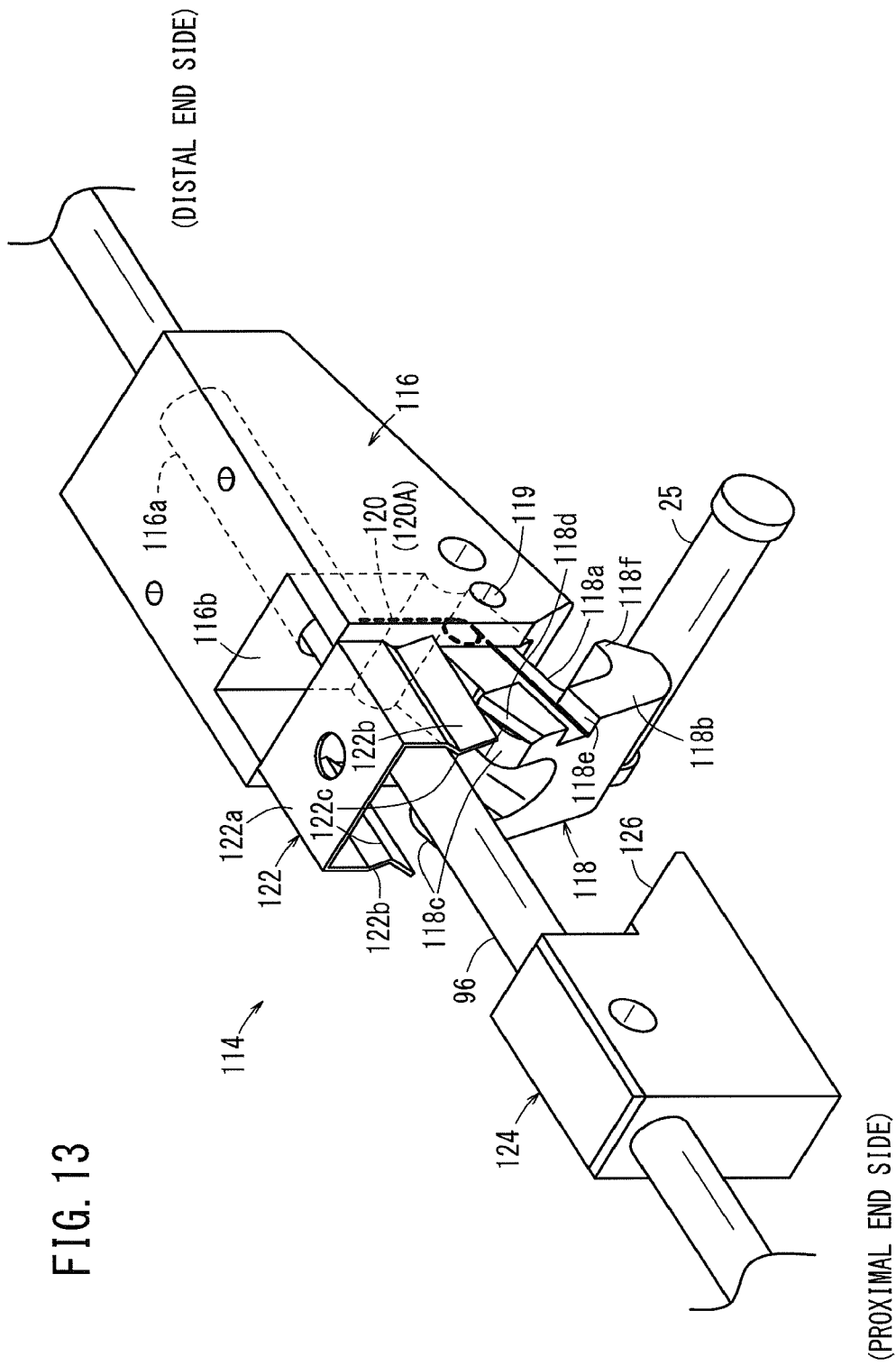
FIG. 13 is a perspective view of a lock mechanism.

As shown in FIGS. 3 and 13, in the medical manipulator 10 according to the present embodiment, a lock mechanism 114 is provided, which is capable of locking the lever 24 at a predetermined position with respect to the body portion 23, and also is capable of releasing the locked condition applied to the lever 24. More specifically, the lock mechanism 114 is constituted to maintain the position (posture) of the lever 24 with respect to the body portion 23, when the lever 24 has come to a position to close the end effector 12.

As shown in FIG. 13, in the present embodiment, the lock mechanism 114 includes a hook holder 116, which is fixed on a lower part of the body portion 23 of the handle main body 20, a hook member 118, which is supported rotatably by the hook holder 116, an elastic member 120 that biases the hook member 118 toward the side of the lever 24, and a holding part 122 that engages with the hook member 118 and holds the hook member 118 when the hook member 118 has been rotated to a predetermined position. A through hole 116a that penetrates along the longitudinal direction of the body portion 23 is formed in the hook holder 116, and the lever rod 96 is inserted for displacement in forward and rearward directions through the through hole 116a.

The hook member 118 is a member that is supported rotatably by a shaft 119 at the proximal end side of the hook holder 116. The hook member 118 is engageable with an engagement pin 25 provided on the lever 24 when the lever 24 arrives at a predetermined position (referred to below as a "first position"). The hook member 118 includes a base portion 118a including the shaft 119, a hook 118b that extends downward from the proximal end side of the base portion 118a, and left and right engaging parts 118c that extend upwardly from the proximal end side of the base portion 118a.

In the present embodiment, the elastic member 120 is constituted in the form of a torsion spring 120A, one end of which engages in a recess 116b disposed on the proximal end side of the hook holder 116, and the other end of which engages in a transverse groove 118e disposed in the hook member 118. In this condition, the hook member 118 normally is biased elastically toward the side of the lever 24 (downwardly). Upon abutment between the bottom of the recess 116b provided in the hook holder 116 and the lower surface of the base portion 118a of the hook member 118, further downward rotation of the hook member 118 is restricted.

The holding part 122 includes a base plate 122a fixed to the body portion 23, and left and right arms 122b that extend downward from both left and right ends of the base plate 122a. Engaging projections 122c formed with inwardly projecting shapes are provided on the respective arms 122b. When the hook member 118 is rotated to a second position (a position at which the hook member 118 overlaps in the vertical direction with the arms of the holding part), which is closer to the body portion 23 than the first position, the engaging projections 122c and engaging recesses 118d, which are provided on outer surfaces of the engaging parts 118c of the hook member 118, come into engagement with each other, whereby the hook member 118 is held by the holding part 122. In a condition in which the hook member 118 is held by the holding part 122, the lever 24 can be disengaged from the hook member 118.

The lock mechanism 114 further includes a releasing member 124. When the lever 24 is displaced in a direction to separate away from the body portion 23, in a state in which the hook member 118 is held by the holding part 122, the releasing member 124 is displaced in conjunction with movement of the lever 24, and by coming into abutment against the hook member 118, causes the hook member 118 to disengage from the holding part. In the present embodiment, the releasing member 124 is fixed to the lever rod 96 more rearwardly than the hook member 118, and is moved integrally with the lever rod 96 in forward and rearward directions when the lever rod 96 is displaced in forward and rearward directions. A butting portion 126 is disposed on the distal end side of the releasing member 124. The butting portion 126 butts against the hook member 118 when the lever 24 is displaced in a direction away from the body portion 23, in a state in which the hook member 118 is held by the holding part 122.

Figure 14A:
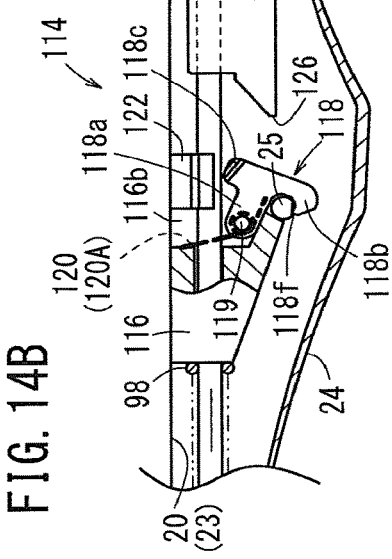
FIG. 14A is a view showing the lock mechanism in an initial condition.
Figure 14B:
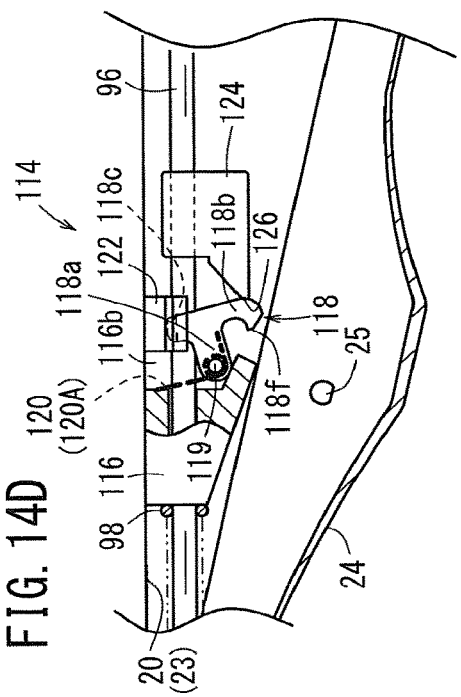
FIG. 14B is a view showing a condition in which a hook member and a lever are engaged.

With the lock mechanism 114, which is constructed in the above-described manner, the following actions are carried out. In FIG. 14A, the lever 24 is at a downwardmost (opened) position with respect to the body portion 23, the hook member 118 also is in a downwardmost position, and the releasing member 124 is at a maximally advanced position. From the condition shown in FIG. 14A, when the lever 24 is pulled inward toward the body portion 23, by the engagement pin 25 that is disposed on the lever 24 pressing a jaw portion 118f of the hook 118b of the hook member 118, the hook member 118 is rotated (upwardly) to the side of the body portion 23 in opposition to the elastic force of the torsion spring 120A. In addition, as shown in FIG. 14B, when the engagement pin 25 rides over the jaw portion 118f, the engagement pin 25 is placed in engagement with the hook 118b. Although the lever 24 is biased elastically by the compression spring 98 in a direction to open with respect to the body portion 23, in the condition in which the engagement pin 25 is engaged with the hook 118b, the lever 24 cannot move in the opening direction. Consequently, even if the user releases his or her hand from the lever 24, the position of the lever 24 with respect to the body portion 23 is maintained. In other words, locking is performed with respect to the lever 24.

In this manner, by locking the position of the lever 24 in a condition in which the target object has been gripped by the end effector 12, even if the hand of the user is released from the lever 24, gripping of the target object by the end effector 12 can be maintained. Thus, the operational burden on the user can be reduced.

Figure 14C:
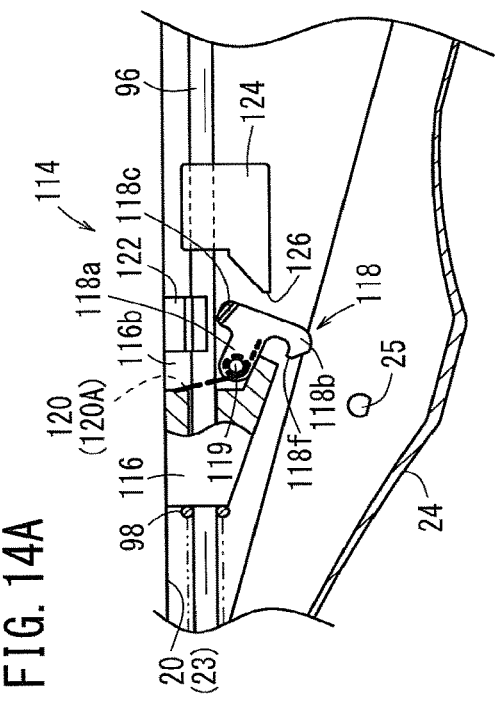
FIG. 14C is a view showing a condition in which the hook member and a retaining member are engaged.

As shown in FIG. 14C, when the lever 24 is pulled further in the closing direction, as a result of the hook member 118 being pressed upward by the engagement pin 25, the engaging parts 118c of the hook member 118 and the holding part 122 come into engagement with each other. Since the engagement force between the holding part 122 and the engaging parts 118c is greater than the elastic force of the torsion spring 120A, the hook member 118 is not pressed downward by the torsion spring 120A. In a condition in which the hook member 118 is held by the holding part 122, the engagement pin 25 of the lever 24 can be disengaged from the hook member 118. Consequently, when the user releases his or her hand from the lever 24, the lever 24 descends and can be restored to its original position (see FIG. 14A).

In this manner, from the locked condition of the lever 24, since engagement between the hook member 118 and the lever 24 can be released merely by operating the lever 24 to approach further toward the body portion 23, locking of the lever 24 can swiftly and easily be released.

Figure 14D:
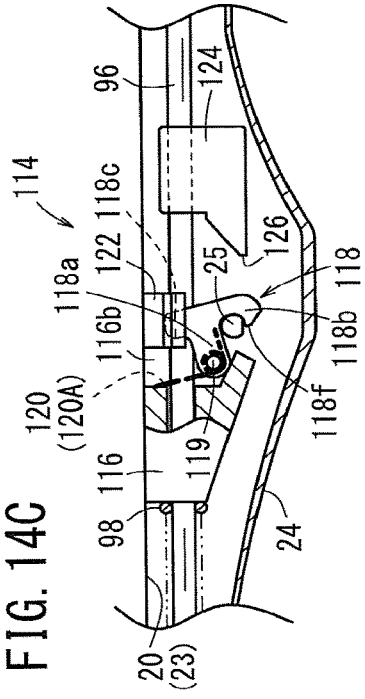
FIG. 14D is a view showing a condition in which a releasing member has just come into abutment against the hook member.

After the engaged state between the engagement pin 25 of the lever 24 and the hook member 118 has been released, the releasing member 124 and the lever rod 96 move forward during the process of lowering the lever 24. In addition, as shown in FIG. 14D, when the butting portion 126 of the releasing member 124 comes into abutment against the hook member 118 and the hook member 118 is pushed forward, the hook member 118 is rotated downward, whereby the engagement between the holding part 122 and the hook member 118 is released. As a result, under a biasing action from the torsion spring 120A, the hook member 118 returns to the original position shown in FIG. 14A.

In this manner, after the engagement between the lever 24 and the hook member 118 is released, merely by the lever 24 being moved in a direction away from the body portion 23, the engagement between the holding part 122 and the hook member 118 is released automatically, and the hook member 118 can be restored quickly to its initial position. Thus, there is no need to carry out an operation to return the hook member 118 to the initial position, and operability thereof is excellent.

Next, primarily with reference to FIGS. 3 and 6, a mechanism will be described in relation to the rolling operation of the distal end working unit 14. In the present embodiment, the rolling operation of the distal end working unit 14 is carried out by transmitting a driving force of the motor 38 to the distal end working unit 14. A rolling operation drive system for causing the distal end working unit 14 to undergo a rolling operation comprises the aforementioned motor 38, the drive gear 40 that is fixed to the motor 38, the driven gear 128 that is enmeshed with the drive gear 40, a rolling drive transmission pipe 130 to which the driven gear 128 is fixed, the bevel gear 86 that is enmeshed with the distal end of the rolling drive transmission pipe 130, and the rotating sleeve 56 that is enmeshed with the bevel gear 86. In the present embodiment, the rolling drive transmission pipe 130 is constituted by the gear member and the hollow shaft 89. Further, the rotating drive transmission part 132, which transmits the rotary driving force from the handle 16 to the distal end working unit 14, is constituted from the rolling drive transmission pipe 130 (see FIGS. 3 and 7), the bevel gear 86, and the rotating sleeve 56.

The drive unit 22 is mounted on the handle main body 20, and in a state in which the controller 44 is connected to a power source, when the rolling switch 28 shown in FIG. 3 is operated by pressing, the motor 38 rotates, and a driving force from the motor 38 is transmitted to the distal end working unit 14 through the drive gear 40, the driven gear 128, the rolling drive transmission pipe 130, the bevel gear 86, and the rotating sleeve 56. As a result, a rolling operation of the distal end working unit 14 is carried out.

With the medical manipulator 10 according to the present embodiment, transmission of the rotational force from the handle 16 to the distal end working unit 14 is not carried out through a wire and a pulley, but rather is carried out through the rolling drive transmission pipe 130 etc. Therefore, the distal end working unit 14 can be operated to roll over an unlimited range of rotation. Further, because the opening and closing drive transmission part 80 (the pull wire 70 and the pull rod 91) is inserted through the rolling drive transmission pipe 130, the opening and closing driving force can be transmitted appropriately to the end effector 12 without being influenced by rotation of the rolling drive transmission pipe 130.

Furthermore, as shown in FIG. 6, since the portion (the pull wire 70) of the opening and closing drive transmission part 80 corresponding to the joint 17 is flexible, with a simple structure, the opening and closing driving force can be transmitted appropriately to the end effector 12. Thus, according to the medical manipulator 10, without increasing the complexity of the mechanism of the distal end working unit 14, a structure can be maintained that enables the opening and closing operation as well as the tilting operation of the distal end working unit 14, while also realizing a rolling operation having an unlimited range of rotation.

Next, a mechanism related to the tilting operation of the distal end working unit 14 will be described. FIG. 15 is a perspective view of the handle 16. In FIG. 15, for facilitating understanding of the structure thereof, the upper cover 29a and the tilt wheel 26 are shown with imaginary lines. The body portion 23 of the handle main body 20 includes a handle 16 frame accommodated in the interior of the casing 29. The handle 16 frame includes a first frame 134, a second frame 136, and a third frame 138.

The first frame 134 is disposed on the distal end side of the body portion 23, and to an upper part thereof, the rolling switch 28 is attached. The second frame 136 is disposed adjacently behind the first frame 134. The third frame 138 is disposed adjacently behind the second frame 136.

A first drive shaft 140 is fixed to the tilt wheel 26, and the tilt wheel 26 and the first drive shaft 140 rotate together integrally. The first drive shaft 140 is supported rotatably on the upper cover about a vertical axis and includes a first gear 141. The first gear 141 meshes with a second gear 143 disposed on a second drive shaft 142. The second drive shaft 142 is arranged on the second frame 136 in parallel with the first drive shaft 140, and includes, on the same axis, a second gear 143 and a worm gear 144. The second gear 143 and the worm gear 144 rotate together integrally. A rotating body 146 including a worm wheel 147 that meshes with the worm gear 144 is arranged rotatably on the second frame 136 about a left-right axis of the body portion 23.

Figure 16:
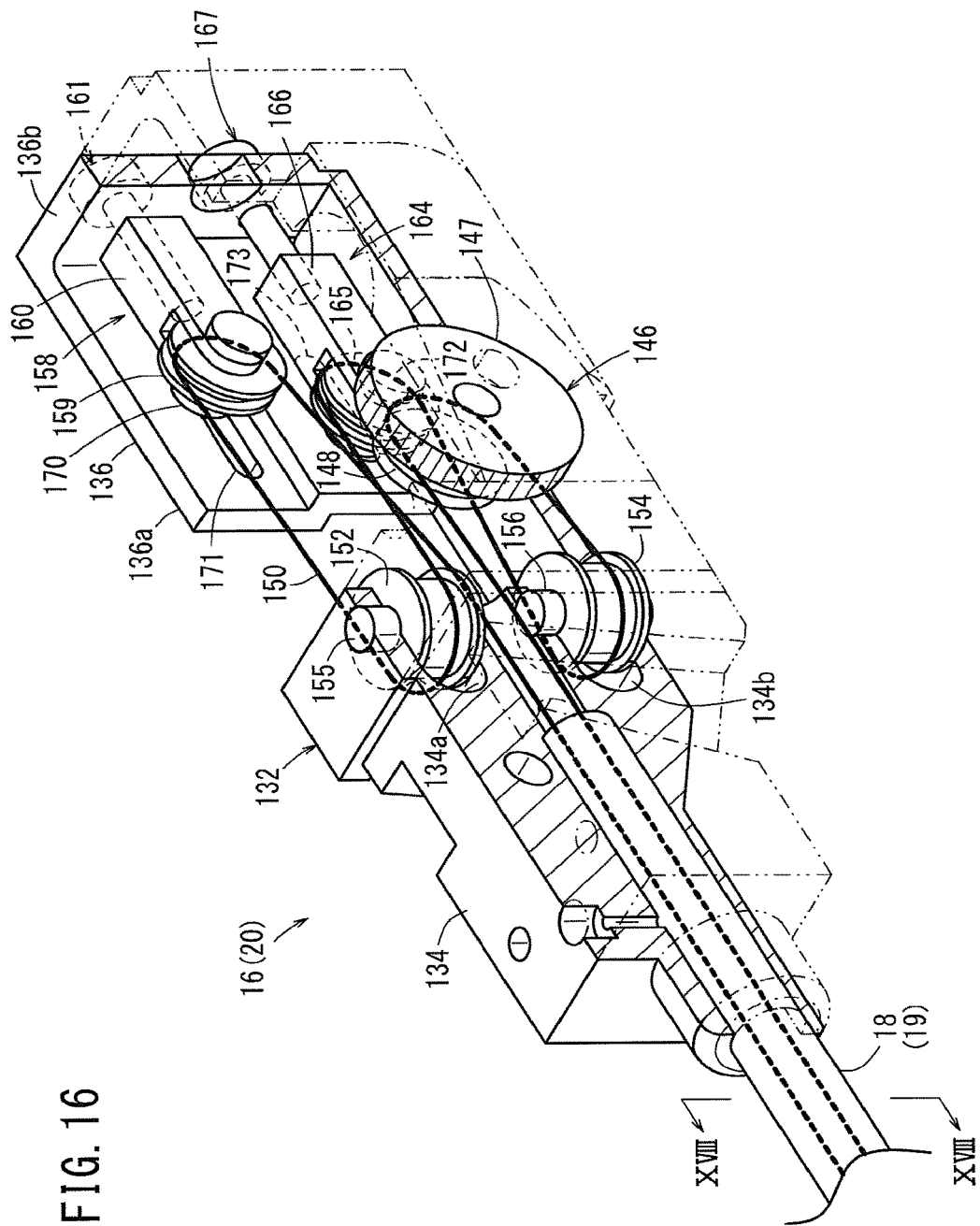
FIG. 16 is a perspective view of a wire arrangement structure on the side of the handle.
Figure 17:
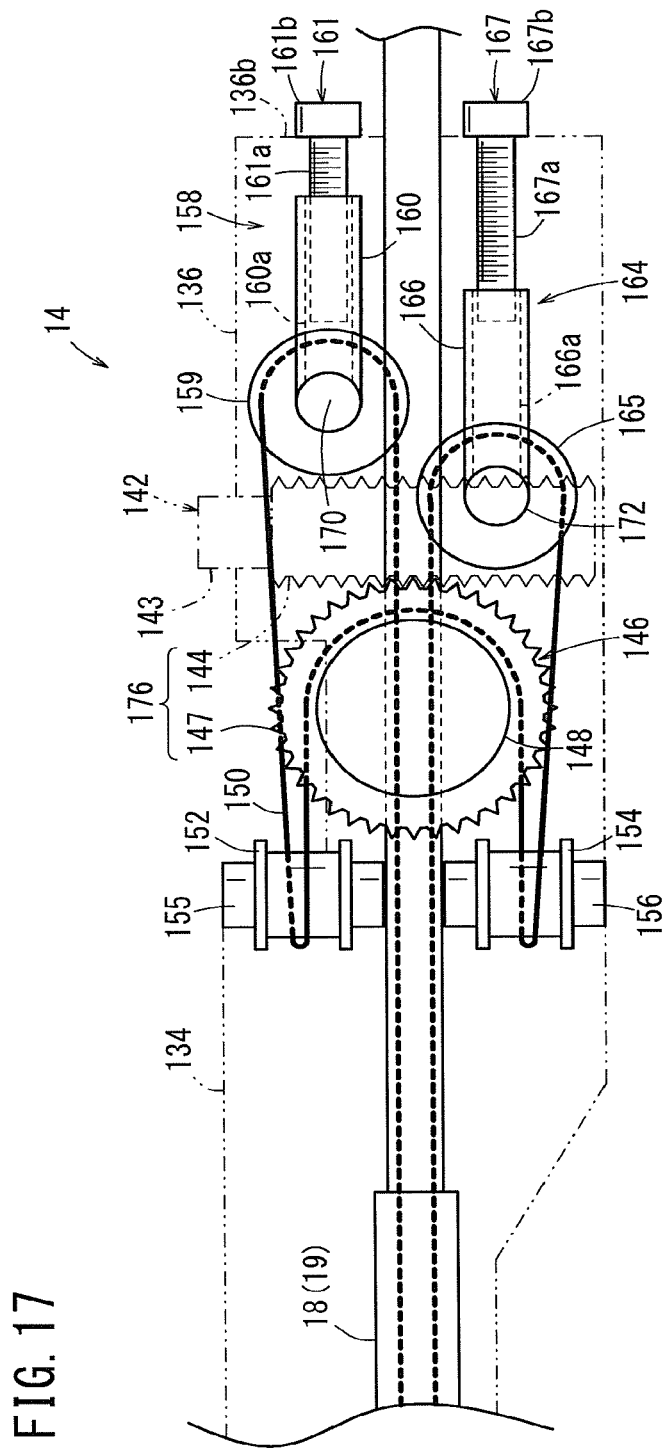
FIG. 17 is a schematic diagram of the wire arrangement structure on the side of the handle.

FIG. 16 is a perspective view (partially shown in cross section) showing a wire arrangement structure on the side of the handle 16. FIG. 17 is a schematic diagram of the wire arrangement structure on the side of the handle 16.

The rotating body 146 includes a worm wheel 147 and a drive pulley 148, which are disposed coaxially. The worm wheel 147 and the drive pulley 148 rotate together in unison. The wire 150 is trained around the drive pulley 148, and the wire 150 further is inserted through the interior of the shaft 18 and is trained around the driven pulley 90 (see FIG. 6) at the distal end side of the shaft 18.

A first intermediate pulley 152 and a second intermediate pulley 154 are arranged in the handle main body 20 on the distal end side (front) of the drive pulley 148, with the wire 150 being trained around the first intermediate pulley 152 and the second intermediate pulley 154. The first intermediate pulley 152 and the second intermediate pulley 154 are supported rotatably on the first frame 134 about vertical axes by respective pins 155, 156. In the first frame 134, installation grooves 134a, 134b, which open toward the proximal end side, are arrayed vertically for arrangement therein of the first intermediate pulley 152 and the second intermediate pulley 154.

In the present embodiment, a first tension mechanism 158 for applying a tensile force to one side portion of the wire 150 between the drive pulley 148 and the driven pulley 90, and a second tension mechanism 164 for applying a tensile force to another side portion of the wire 150 between the drive pulley 148 and the driven pulley 90, are disposed in the handle 16. The first tension mechanism 158 is equipped with a first tension pulley 159 around which the wire 150 is trained, a first holding portion 160 that supports the first tension pulley 159 and is capable of being displaced, and a first adjustment member 161 for adjusting and positioning the position of the first holding portion 160. Similarly, the second tension mechanism 164 is equipped with a second tension pulley 165 around which the wire 150 is trained, a second holding portion 166 that supports the second tension pulley 165 and is capable of being displaced, and a second adjustment member 167 for adjusting and positioning the position of the second holding portion 166.

On the handle main body 20, the first tension pulley 159 and the second tension pulley 165 are disposed on the proximal end side (rearwardly) of the drive pulley 148. The first tension pulley 159 and the second tension pulley 165 are supported rotatably about respective left-right axes. More specifically, the first tension pulley 159 is supported rotatably by a support shaft 170 on a distal end of the first holding portion 160, and the support shaft 170 is guided slidably in forward and rearward directions in a long hole 171 that extends in the front-back direction and is provided in a side wall 136a of the second frame 136. Similarly, the second tension pulley 165 is supported rotatably by a support shaft 172 on a distal end of the second holding portion 166, and the support shaft 172 is guided slidably in forward and rearward directions in a long hole 173 that extends in the front-back direction and is provided in the side wall 136a of the second frame 136.

As shown in FIG. 17, a screw hole 160a is provided in the first holding portion 160, and a threaded rod 161a of the first adjustment member 161 is screw-engaged into the screw hole 160a. The head 161b of the first adjustment member 161 is greater in diameter than the threaded rod 161a. The threaded rod 161a of the first adjustment member 161 is inserted from the rear in a through hole that is provided in a rear wall 136b of the second frame 136, and the head 161b abuts against the rear wall 136b. When the first adjustment member 161 is rotated, the first holding portion 160 is moved in forward and rearward directions by a screwing action. Accordingly, by adjusting the position of the first tension pulley 159 that is supported by the first holding portion 160, the tensile force that is applied to the one side portion of the wire 150 between the drive pulley 148 and the driven pulley 90 can be adjusted.

A screw hole 166a is provided in the second holding portion 166, and a threaded rod 167a of the second adjustment member 167 is screw-engaged into the screw hole 166a. The head 167b of the second adjustment member 167 is greater in diameter than the threaded rod 167a. The threaded rod 167a of the second adjustment member 167 is inserted from the rear in a through hole that is provided in the rear wall 136b of the second frame 136, and the head 167b abuts against the rear wall 136b. When the second adjustment member 167 is rotated, the second holding portion 166 is moved in forward and rearward directions by a screwing action. Accordingly, by adjusting the position of the second tension pulley 165 that is supported by the second holding portion 166, the tensile force that is applied to the other side portion of the wire 150 between the drive pulley 148 and the driven pulley 90 can be adjusted.

Figure 18:
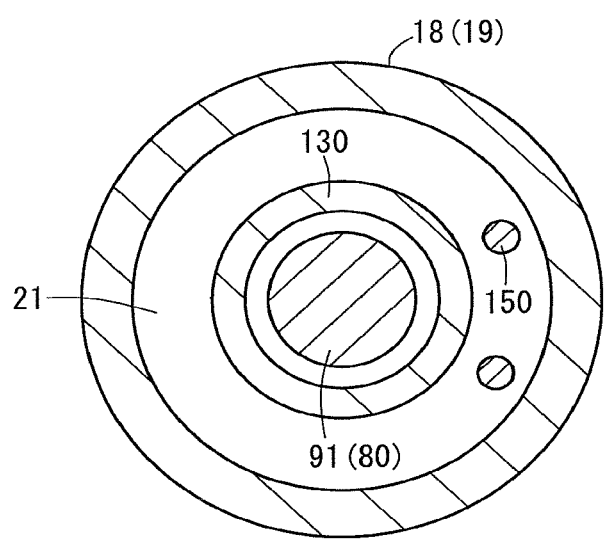
FIG. 18 is a cross sectional view taken along line XVIII-XVIII of FIG. 16.

FIG. 18 is a cross sectional view taken along line XVIII-XVIII of FIG. 16. As shown in FIG. 18, an annular space 21 that extends along the axis of the shaft 18 is disposed between the shaft 18 and the rolling drive transmission pipe 130, and the wire 150 is inserted through the annular space 21. As described above, the wire 150 is trained around the driven pulley 90 (see FIG. 6), which is arranged at the distal end of the shaft 18.

As shown in FIG. 5, at different positions in the circumferential direction on the distal end inner circumferential surface of the shaft main body 19, two guide grooves 19a are provided for guiding the wire 150. Further, on the shaft side fulcrum block 59 that is fixed to the distal end of the shaft main body 19, two guide holes 59d through which the wire 150 is slidably inserted are provided at different positions in the circumferential direction. The guide holes 59d penetrate in the axial direction through the tubular portion 59a of the shaft side fulcrum block 59. As shown in FIG. 9, the wire 150 is trained around the driven pulley 90 at a portion thereof that is pulled out from the two guide holes 59d.

Next, the mechanism related to the tilting operation, which is constructed in the foregoing manner, will be described. When the rotating operation of the tilt wheel 26 shown in FIG. 15 is carried out manually, the operating force thereof is transmitted to the first drive shaft 140, the second drive shaft 142, and the rotating body 146. The rotational force transmitted to the rotating body 146 drives the wire 150, which is trained around the drive pulley 148 provided on the rotating body 146. In this case, one side portion of the wire 150 between the drive pulley 148 and the driven pulley 90 is trained around the first intermediate pulley 152 and the first tension pulley 159, whereas the other side portion of the wire 150 between the drive pulley 148 and the driven pulley 90 is trained around the second intermediate pulley 154 and the second tension pulley 165, and in a condition in which tensile forces are applied, driving is carried out corresponding to the rotation of the drive pulley 148. Driving of the wire 150 is output at the distal end of the shaft 18 so that the driven pulley 90 is rotated, whereby the tilting operation of the distal end working unit 14 with respect to the shaft 18 is carried out.

The medical manipulator 10 according to the present embodiment is equipped with the first tension mechanism 158 and the second tension mechanism 164. In accordance therewith, concerning one side and the other side of the wire 150 between the drive pulley 148 and the driven pulley 90, tensile forces can be applied separately with respect to the wire 150, and an appropriate tensile force can be applied appropriately to the wire 150 as a whole. Consequently, the distal end working unit 14 responds precisely and accurately with respect to operations of the user, and excellent operability can be obtained.

Further, the first tension mechanism 158 and the second tension mechanism 164 are equipped respectively with the tension pulleys 159, 165, the holding portions 160, 166, and the adjustment members 161, 167. Therefore, tensile forces of the wire 150 can be adjusted separately concerning one side and the other side of the wire 150 between the drive pulley 148 and the driven pulley 90. Thus, power transmission from the drive pulley 148 to the driven pulley 90 can be performed appropriately through the wire 150.

Furthermore, with the medical manipulator 10 according to the present embodiment, since the two tension pulleys 159, 165 and the two intermediate pulleys 152, 154 are arranged on front and rear sides with respect to the drive pulley 148, the wire 150 can be arranged efficiently in the interior of the handle 16, and a small sized handle 16 can be constructed.

In the medical manipulator 10, on the handle 16 thereof, a manual manipulating element for carrying out a manual operation with respect to one of the tilting operation and the rolling operation of the distal end working unit 14, an electrical manipulating element for giving instructions for performing the other of the tilting operation and the rolling operation, and a drive source that operates based on operations made with respect to the electrical manipulating element are provided. The operating force of the user with respect to the manual manipulating element is transmitted mechanically to the distal end working unit 14 through a first power transmission path, and the driving force of the drive source is transmitted to the distal end working unit 14 through a second power transmission path. Further, a one-way power transmission mechanism 176 is provided midway along the first power transmission path, which is constructed such that, although power can be transmitted to the distal end working unit 14 from the manual operating element, power cannot be transmitted in the opposite direction.

With the present embodiment, the tilt wheel 26 corresponds to the above-described manual manipulating element, and the rolling switch 28 corresponds to the above-described electrical manipulating element. The motor 38 corresponds to the above-described drive source. Further, the power transmission path (the second drive shaft 142, the rotating body 146, the wire 150, etc.) between the tilt wheel 26 and the distal end working unit 14 corresponds to the above-described first power transmission path, and the power transmission path (the rolling drive transmission pipe 130, etc.) between the motor 38 and the distal end working unit 14 corresponds to the above-described second power transmission path.

Further, differing from the present embodiment, in the case that a structure is adopted in which the tilting operation is carried out by an electrical drive, and the rolling operation is carried out by a manual drive, the power transmission path between the distal end working unit 14 and the manual manipulating element for the rolling operation corresponds to the above-described first power transmission path, and the power transmission path between the distal end working unit 14 and the drive source that is operated based on the electrical manipulating element for the tilting operation corresponds to the above-described second power transmission path.

As shown in FIG. 17, in the present embodiment, the one-way power transmission mechanism 176 is constituted from the aforementioned worm gear 144 and worm wheel 147. In the first power transmission path, the worm wheel 147 is arranged on the side of the distal end working unit 14 relative to the worm gear 144.

With the medical manipulator 10 equipped with the one-way power transmission mechanism 176, when the distal end working unit 14 is operated based on the rolling switch 28, although the distal end working unit 14 receives a force in a direction of the tilting action due to interference in the mechanism of the distal end working unit 14, transmission of the force from the distal end working unit 14 to the tilt wheel 26 is interrupted by the one-way power transmission mechanism 176. Therefore, when the distal end working unit 14 is operated based on the rolling switch 28, even if the tilt wheel 26 is not manually fixed in place by the user, the distal end working unit 14 is not affected by interfering operations, and operability is excellent.

With the medical manipulator 10, a structure is adopted in which the rolling operation is carried out by an electrical drive, whereas the tilting operation is carried out through a manual drive, and thus, a reduction in size and weight of the medical manipulator 10 is realized. Hypothetically, in the case that the rolling operation and the tilting operation were both carried out through electrical drives, the aforementioned interfering operations could be prevented by a motor control or a large gear ratio (geared motor). However, in the case of a structure in which one of the rolling operation and the tilting operation is carried out by a manual drive whereas the other operation is carried out by an electrical drive, an interfering operation prevention means cannot be obtained using a large gear ratio (geared motor) or a motor control.

In contrast thereto, in the medical manipulator 10, in addition to reducing the size and weight by mounting of only one motor 38 therein, by providing the aforementioned one-way power transmission mechanism 176, the above-described interfering operations can be prevented.

Although a certain preferred embodiment of the present invention has been shown and described in detail above, it should be understood that various changes and modifications may be made to the embodiment without departing from the scope of the invention as set forth in the appended claims.

What is claimed is:

1. A medical manipulator comprising:
   a handle;
   a shaft that extends from the handle;
   a distal end working unit having an end effector capable of performing an opening and closing operation, and which is connected tiltably with respect to the shaft, and further which is capable of performing a rolling operation;
   an opening and closing drive transmission part that transmits a driving force for performing the opening and closing operation from the handle to the distal end working unit; and
   a rotating drive transmission part for transmitting a rotational force for performing the rolling operation from the handle to the distal end working unit,
   wherein:
   the rotating drive transmission part includes a rolling drive transmission pipe, an intermediate member and a distal end side rotating body that interact with one another to perform the rolling operation of the distal end working unit, the rolling drive transmission pipe extends along a direction of extension of the shaft and is rotatably disposed in an interior of the shaft, the intermediate member is disposed in a joint between the shaft and the distal end working unit, meshes with the rolling drive transmission pipe, and is rotatable about a tilting fulcrum of the distal end working unit, and the distal end side rotating body is disposed in the distal end working unit, meshes with the intermediate member, and is rotatable about a roll axis; and
   the opening and closing drive transmission part is disposed inside the rolling drive transmission pipe, and a portion of the opening and closing drive transmission part that is inserted at least through the joint is flexible; and
   in the vicinity of the tilting fulcrum of the distal end working unit with respect to the shaft, guide members guide the opening and closing drive transmission part such that the guide members are configured to suppress unintentional driving of the opening and closing drive transmission part when the distal end working unit is articulated relative to the shaft, the guide members being disposed on both sides of the opening and closing drive transmission part in a tilting direction of the distal end working unit.

2. The medical manipulator according to claim 1, wherein:
   the opening and closing drive transmission part is capable of making advancing and retracting movements with respect to the shaft, and the end effector performs the opening and closing operation by the advancing and retracting movements.

3. The medical manipulator according to claim 2, wherein the guide members are guide rollers.

4. The medical manipulator according to claim 1, wherein:
   the joint includes a pair of joint pins disposed on a tilt axis; and
   the opening and closing drive transmission part is configured to advance and retract in a direction intersecting an axial direction of the joint pins, through a gap that is provided between the pair of joint pins.

5. The medical manipulator according to claim 1, wherein the opening and closing drive transmission part has a proximal end which extends into the handle, the opening and closing drive transmission part being substantially linear from the flexible portion of the opening and closing drive transmission part to the proximal end of the opening and closing drive transmission part.

6. The medical manipulator according to claim 1, wherein the distal end working unit includes a link member and a transmission member, the link member being rotatably connected to the end effector and the transmission member being rotatably connected to the link member; and
wherein the link member and the transmission member pivot relative to one another in response to receiving the driving force from the opening and closing drive transmission part.

7. The medical manipulator according to claim 6, wherein a distal end of the opening and closing drive transmission part comprises an end collar; and
wherein a distal end of the end collar comprises a bulge which engages with a distal side of the transmission member of the distal end working unit, the transmission member being configured to move in a proximal direction when the opening and closing drive transmission part and the end collar are retracted away from the end effector.

8. The medical manipulator according to claim 7, wherein at least a proximal portion of the end collar is inserted in the transmission member.

9. The medical manipulator according to claim 7, further comprising a compression spring disposed between the transmission member of the distal end working unit and the distal end side rotating body of the rotating drive transmission part.

10. The medical manipulator according to claim 9, wherein:
the distal side of the transmission member includes a flange;
the distal end side rotating body includes a stepped portion; and
one end of the compression spring abuts against the flange and the other end of the compression spring abuts against the stepped portion so that the transmission member is biased in a distal direction.

11. The medical manipulator according to claim 10, wherein the stepped portion is disposed on an inner circumferential surface of the distal end side rotating body.

12. The medical manipulator according to claim 1, wherein the opening and closing drive transmission part comprises a wire; and
wherein the end effector opens when the wire is retracted in a proximal direction and closes when the wire is advanced in a distal direction.

13. The medical manipulator according to claim 1, wherein the tilting fulcrum comprises a pulley supported rotatably by a joint pin which is disposed on a tilt axis; and
wherein a tilt operation wire is fixed to the pulley and extends through the shaft to the handle for rotating the pulley.

14. The medical manipulator according to claim 1, wherein a proximal end of the rolling drive transmission pipe extends into the handle.

15. A medical manipulator comprising:
a handle;
a shaft that extends from the handle;
a distal end working unit having an end effector capable of performing an opening and closing operation, and which is connected tiltably with respect to the shaft via a tilting fulcrum, and further which is capable of performing a rolling operation;
an opening and closing drive transmission part that transmits a driving force for performing the opening and closing operation from the handle to the distal end working unit;
a rotating drive transmission part configured to transmit a rotational force for performing the rolling operation from the handle to the distal end working unit;
the rotating drive transmission part having a rolling drive transmission pipe, an intermediate member and a distal end side rotating body that interact with one another to perform the rolling operation of the distal end working unit, the rolling drive transmission pipe extends along a direction of extension of the shaft and is rotatably disposed in an interior of the shaft, the intermediate member is disposed in a joint between the shaft and the distal end working unit, meshes with the rolling drive transmission pipe, and is rotatable about a tilt axis of the tilting fulcrum, and the distal end side rotating body is disposed in the distal end working unit, meshes with the intermediate member, and is rotatable about a roll axis;
the opening and closing drive transmission part being disposed inside the rolling drive transmission pipe, and a portion of the opening and closing drive transmission part that is inserted at least through the joint is flexible; and
two guide members being disposed in a vicinity of the tilting fulcrum on both sides of the opening and closing drive transmission part and being rotatable about axes parallel to the tilt axis of the tilting fulcrum, wherein the portion of the opening and closing drive transmission part that is flexible bends around only a first guide member in response to the distal end working unit being tilted in a first direction and bends around only a second guide member in response to the distal end working unit being tilted in a second direction which is opposite the first direction.

* * * * *